US010702576B2

(12) United States Patent
Mo et al.

(10) Patent No.: US 10,702,576 B2
(45) Date of Patent: Jul. 7, 2020

(54) STABLE FORMULATIONS OF LINACLOTIDE

(71) Applicants: Ironwood Pharmaceuticals, Inc., Cambridge, MA (US); Forest Laboratories Holdings Limited, Hamilton (BM)

(72) Inventors: Yun Mo, Commack, NY (US); Angelika Fretzen, Somerville, MA (US); Brian Cali, Arlington, MA (US); Mahendra Dedhiya, Pomona, NY (US)

(73) Assignees: IRONWOOD PHARMACEUTICALS, INC., Cambridge, MA (US); FOREST LABORATORIES HOLDINGS LIMITED, Hamilton (BM)

( * ) Notice: Subject to any disclaimer, the term of this patent is extended or adjusted under 35 U.S.C. 154(b) by 0 days.

(21) Appl. No.: 16/250,237

(22) Filed: Jan. 17, 2019

(65) Prior Publication Data
US 2019/0209644 A1    Jul. 11, 2019

Related U.S. Application Data

(63) Continuation of application No. 16/006,070, filed on Jun. 12, 2018, now abandoned, which is a continuation of application No. 15/727,700, filed on Oct. 9, 2017, now abandoned, which is a continuation of application No. 15/439,049, filed on Feb. 22, 2017, now abandoned, which is a continuation of application No. 15/203,951, filed on Jul. 7, 2016, now abandoned, which is a continuation of application No. 14/948,795, filed on Nov. 23, 2015, now abandoned, which is a continuation of application No. 14/689,561, filed on Apr. 17, 2015, now abandoned, which is a continuation of application No. 14/484,568, filed on Sep. 12, 2014, now abandoned, which is a continuation of application No. 13/816,154, filed as application No. PCT/US2011/047434 on Aug. 11, 2011, now abandoned.

(60) Provisional application No. 61/372,804, filed on Aug. 11, 2010.

(51) Int. Cl.
| | |
|---|---|
| A61K 38/10 | (2006.01) |
| A61P 1/00 | (2006.01) |
| A61K 38/12 | (2006.01) |
| A61K 9/16 | (2006.01) |
| A61K 47/18 | (2017.01) |

(52) U.S. Cl.
CPC ........... *A61K 38/12* (2013.01); *A61K 9/1611* (2013.01); *A61K 9/1641* (2013.01); *A61K 9/1676* (2013.01); *A61K 38/10* (2013.01); *A61K 47/18* (2013.01)

(58) Field of Classification Search
None
See application file for complete search history.

(56) References Cited

U.S. PATENT DOCUMENTS

| | | | |
|---|---|---|---|
| 4,544,568 | A | 10/1985 | Heyland et al. |
| 4,545,931 | A | 10/1985 | Houghton |
| 4,806,524 | A | 2/1989 | Kawaguchi |
| 4,992,419 | A | 2/1991 | Woog et al. |
| 5,130,298 | A | 7/1992 | Cini et al. |
| 5,221,495 | A | 6/1993 | Cao |
| 5,451,410 | A | 9/1995 | Milstein |
| 5,489,670 | A | 2/1996 | Currie et al. |
| 5,518,888 | A | 5/1996 | Waldman |
| 5,593,696 | A | 1/1997 | McNally et al. |
| 5,654,278 | A | 8/1997 | Sorensen |
| 5,672,359 | A | 9/1997 | Digenis et al. |
| 5,705,537 | A | 1/1998 | Hartman et al. |
| 5,874,106 | A | 2/1999 | Adesunloye et al. |
| 5,904,935 | A | 5/1999 | Eckenhoff et al. |
| 5,969,097 | A | 10/1999 | Wiegand et al. |
| 5,980,945 | A | 11/1999 | Ruiz |
| 6,022,858 | A | 2/2000 | Sorensen et al. |
| 6,068,850 | A | 5/2000 | Stevenson et al. |
| 6,124,261 | A | 9/2000 | Stevenson et al. |
| 6,383,788 | B1 | 5/2002 | Chan et al. |
| 6,541,606 | B2 | 4/2003 | Margolin et al. |
| 6,734,162 | B2 | 5/2004 | Van Antwerp |
| 6,828,303 | B2 | 12/2004 | Kim et al. |
| 6,979,437 | B2 | 12/2005 | Bartus |
| 6,995,200 | B2 | 2/2006 | Krohnke |

(Continued)

FOREIGN PATENT DOCUMENTS

| | | |
|---|---|---|
| EP | 0943336 | 9/1999 |
| EP | 1559433 | 8/2005 |

(Continued)

OTHER PUBLICATIONS

Linzess® prescribing information, accessed Feb. 18, 2020 at URL:accessdata.fda.gov/drugsatfda_docs/label/2017/202811s013lbl.pdf, 21 pages (Year: 2020).*

Camilleri et al., "Gastrointestinal complications of obesity," Gastroent. 152:1656-1670 (2017) (Year: 2017).*

Aimoto et al., "Chemical Synthesis of a Highly Potent and Heat-Stable Analog of an Enterotoxin Produced by a Human Strain of Enterotoxigenic *Escherichia coli*." Biochem. Biophys. Res. Commun. 112(1):320-326, 1983.

Albano et al., "Structural and functional features of modified heat stable toxins produced by enteropathogenic Klebsiella cells." Pediatric Research 48(5): 685-690, 2000.

(Continued)

*Primary Examiner* — Julie Ha
*Assistant Examiner* — Kristina M Hellman
(74) *Attorney, Agent, or Firm* — Honigman LLP; Kelly T. Murphy; Jonathan P. O'Brien

(57) ABSTRACT

The present invention relates to stable pharmaceutical compositions comprising linaclotide or pharmaceutically acceptable salts thereof, as well as to various methods and processes for the preparation and use of the compositions.

20 Claims, 1 Drawing Sheet
Specification includes a Sequence Listing.

(56) References Cited

U.S. PATENT DOCUMENTS

| | | |
|---|---|---|
| 7,056,942 B2 | 6/2006 | Hildesheim et al. |
| 7,141,254 B2 | 11/2006 | Bhaskaran et al. |
| 7,304,036 B2 | 4/2007 | Currie et al. |
| 7,351,798 B2 | 4/2008 | Margolin et al. |
| 7,371,727 B2 | 5/2008 | Currie et al. |
| 7,494,979 B2 | 2/2009 | Currie et al. |
| 7,704,947 B2 | 4/2010 | Currie et al. |
| 7,745,409 B2 | 6/2010 | Currie et al. |
| 7,767,644 B2 | 8/2010 | Schumann et al. |
| 7,772,188 B2 | 8/2010 | Currie et al. |
| 7,910,546 B2 | 3/2011 | Currie et al. |
| 8,080,526 B2 | 12/2011 | Currie et al. |
| 8,101,579 B2 | 1/2012 | Currie et al. |
| 8,110,553 B2 | 2/2012 | Currie et al. |
| 8,748,573 B2 | 6/2014 | Fretzen et al. |
| 8,802,628 B2 | 8/2014 | Fretzen et al. |
| 2003/0003563 A1 | 1/2003 | Vinkemeier et al. |
| 2003/0069182 A1 | 4/2003 | Rinella |
| 2003/0073628 A1 | 4/2003 | Shailubhai et al. |
| 2003/0104996 A1 | 6/2003 | Li et al. |
| 2003/0175230 A1 | 9/2003 | Dubief |
| 2004/0265242 A1 | 12/2004 | Bartus |
| 2004/0266989 A1 | 12/2004 | Currie |
| 2005/0020811 A1 | 1/2005 | Currie et al. |
| 2005/0080009 A1 | 4/2005 | Metzner et al. |
| 2007/0122354 A1 | 5/2007 | Hastedt et al. |
| 2007/0154406 A1 | 7/2007 | Moon et al. |
| 2007/0202165 A1 | 8/2007 | Heuer et al. |
| 2008/0124326 A1 | 5/2008 | Rehder et al. |
| 2009/0110729 A1 | 4/2009 | Giovannone et al. |
| 2009/0253634 A1 | 10/2009 | Currie et al. |
| 2009/0305993 A1 | 12/2009 | Currie |
| 2010/0048489 A1 | 2/2010 | Fretzen et al. |
| 2010/0221329 A1 | 9/2010 | Shailubhai et al. |
| 2011/0059903 A1* | 3/2011 | Fretzen ............... A61K 9/1611 514/21.1 |
| 2012/0009225 A1 | 1/2012 | Fretzen et al. |
| 2012/0039949 A1 | 2/2012 | Fretzen et al. |
| 2012/0213846 A1 | 8/2012 | Fretzen et al. |
| 2013/0190239 A1 | 7/2013 | Fretzen et al. |
| 2013/0273169 A1 | 10/2013 | Fretzen et al. |
| 2014/0005128 A1 | 1/2014 | Mo et al. |
| 2014/0342996 A1 | 11/2014 | Currie et al. |
| 2014/0348942 A1 | 11/2014 | Currie et al. |
| 2015/0030697 A1 | 1/2015 | Currie et al. |
| 2015/0094272 A1 | 4/2015 | Kessler et al. |

FOREIGN PATENT DOCUMENTS

| | | |
|---|---|---|
| EP | 1908482 | 4/2008 |
| JP | 02-023849 | 6/1988 |
| JP | 64-009938 | 1/1989 |
| JP | 2003-201256 | 7/2003 |
| WO | WO90012029 | 4/1991 |
| WO | WO91004743 | 4/1991 |
| WO | WO97003692 | 2/1997 |
| WO | WO97004796 | 2/1997 |
| WO | WO98000152 | 1/1998 |
| WO | WO98000157 | 1/1998 |
| WO | WO00004880 | 2/2000 |
| WO | WO00032172 | 6/2000 |
| WO | WO01025266 | 4/2001 |
| WO | WO02026248 | 4/2002 |
| WO | WO02062369 | 8/2002 |
| WO | WO02078683 | 10/2002 |
| WO | WO03014304 | 2/2003 |
| WO | WO03055511 | 7/2003 |
| WO | WO04039392 | 5/2004 |
| WO | WO04052343 | 6/2004 |
| WO | WO04108152 | 12/2004 |
| WO | WO05014025 | 2/2005 |
| WO | WO05042029 | 5/2005 |
| WO | WO06088418 | 8/2006 |
| WO | WO07044375 | 4/2007 |
| WO | WO07053390 | 5/2007 |
| WO | WO08006125 | 1/2008 |
| WO | WO08021133 | 2/2008 |
| WO | WO08027854 | 3/2008 |
| WO | WO08078189 | 7/2008 |
| WO | WO08106429 | 9/2008 |
| WO | WO08151257 | 12/2008 |
| WO | WO10019266 | 2/2010 |
| WO | WO10065751 | 6/2010 |
| WO | WO11019819 | 2/2011 |
| WO | WO12021715 | 2/2012 |

OTHER PUBLICATIONS

Appel, "Chymotrypsin: Molecular and Catalytic Properties." Clin Biochem. 19:317-322, 1986.

Del Barrio et al., "Simultaneous determination of formic acid and formaldehyde in pharmaceutical excipients using headspace GC/MS." Journal of Pharmaceutical and Biomedical Analysis, vol. 41, Issue 3, pp. 738-743, Jun. 7, 2006.

Bodmeier et al., "Spherical agglomerates of water—insoluble drugs." Journal of pharmaceutical sciences 78, No. 11: 964-967, 1989.

Bretz et al., "Practical considerations for optimal designs in clinical dose finding studies." Statist. Med., 29: 731-742, 2013.

Bundegaard et al.,"Prodrugs of peptides. 15. 4-Imidazolidinone prodrug derivatives of enkephalins to prevent aminopeptidase-catalyzed metabolism in plasma and absorptive mucosae." International journal of pharmaceutics 76, No. 1-2: 113-122, 1991.

Carpick et al., "Structural characterization of functionally important regions of the *Escherichia coli* heat-stable enterotoxin STIb." Biochemistry, 30 (19), pp. 4803-4809, 1991.

Carpick et al., "The *Escherichia coli* heat-stable enterotoxin is a long-lived superagonist of guanylin." Infection and Immunity, 61: 4710-15, 1993.

Chen, "Formulation concerns of protein drugs." Drug development and industrial pharmacy 18, No. 11-12: 1311-1354, 1992.

Chen et al.,"Influence of calcium ions on the structure and stability of recombinant human deoxyribonuclease I in the aqueous and lyophilized states." J. Pharm. Sci., 88: 477-482, 1999.

Cohen et al., "Age-related differences in receptors for *Escherichia coli* heat-stable enterotoxin in the small and large intestine of children." Gastroenterology 94, No. 2: 367-373, 1988.

Cohen et al., "*E. coli* Heat-Stable Enterotoxin (Sta) Induced Secretion: Differences Between Adult Rat Jejunum and Ileum Correlate with Differences in Metabolic Fate of STa". Advances in Research on Cholera and Related Diarrheas, 7th Ed. pp. 99-104, 1990.

Cohen et al., "Jejunal toxin inactivation regulates susceptibility of the immature rat to Sta." Gastroenterol., 102:1988-96, 1992.

Crowley, "Excipients as stabilizers." Pharmaceutical Science & Technology Today, vol. 2, Issue 6, pp. 237-243, Jun. 1, 1999.

Dahm et al., "Rat jejunum controls luminal thiol-disulfide redox." The Journal of nutrition 130, No. 11: 2739-2745, 2000.

Dayhoff et al., "A model of evolutionary change in proteins." Atlas of Protein Sequence and Structure, 5(supplement 3): 345-352, 1978.

Dreyfus et al., "Solubilization and partial characterization of the intestinal receptor for *Escherichia coli* heat-stable enterotoxin." Infection and immunity 46, No. 2: 537-543, 1984.

Eberle et al., "Rapid oxidation in vitro of endogenous and exogenous glutathione in bile of rats." Journal of Biological Chemistry 256, No. 5: 2115-2117, 1981.

Ewe, "Intestinal transport in constipation and diarrhoea." Pharmacology 36, No. Suppl. 1: 73-84, 1988.

FDA Guidance for Industry, 1994, "Submission of Chemistry, Manufacturing and Controls Information for Synthetic Peptide Substances." Retrieved from http://www.gmp-compliance.org/guidemgr/files/CMC4.PDF.

Fleckenstein et al., "Minute rhythm of electrical spike bursts of the small intestine in different species." American Journal of Physiology-Gastrointestinal and Liver Physiology 242, No. 6: G654-G659, 1982.

Forte et al., "Guanylin regulatory peptides: structures, biological activities mediated by cyclic GMP and pathobiology." Regulatory Peptides 81: 25-39, 1999.

(56) References Cited

OTHER PUBLICATIONS

Frantz et al., "Binding of *Escherichia coli* heat-stable enterotoxin to rat intestinal cells and brush border membranes." Infection and immunity 43, No. 2: 622-630, 1984.
Fujita et al., "Generation of formaldehyde by pharmaceutical excipients and its absorption by meglumine." Chemical and Pharmaceutical Bulletin 57, No. 10: 1096-1099, 2009.
Fyfe et al., "An~ 140-kb deletion associated with feline spinal muscular atrophy implies an essential LIX1 function for motor neuron survival." Genome research 16, No. 9: 1084-1090, 2006.
Gariepy et al., "Structure of the toxic domain of *Escherichia coli* heat-stable enterotoxin ST I." Biochemistry 25, No. 24: 7854-7866, 1986.
Gariepy et al., "Design of a photoreactive analogue of the *Escherichia coli* heat-stable enterotoxin STIb: use in identifying its receptor on rat brush border membranes." Proceedings of the National Academy of Sciences 83, No. 2: 483-487, 1987.
Gariepy et al., "Importance of disulfide bridges in the structure and activity of *Escherichia coli* enterotoxin ST1b." Proceedings of the National Academy of Sciences 84, No. 24: 8907-8911, 1987.
Gennaro, Remington. "The Science and Practice of Pharmacy". Lippincott Williams & Wilkins, 20th Ed., 2000.
Giannella, "*Escherichia coli* heat-stable enterotoxins, guanylins, and their receptors: What are they and what do they do?" The Journal of Laboratory and Clinical Medicine, 125(2): 173-181, 1995.
Greenberg et al., "Reduction of the secretory response to *Escherichia coli* heat-stable enterotoxin by thiol and disulfide compounds." Infection and immunity 41, No. 1: 174-180, 1983.
Greenberg et al., "Comparison of effects of uroguanylin, guanylin, and *Escherichia coli* heat-stable enterotoxin STa in mouse intestine and kidney: evidence that uroguanylin is an intestinal natriuretic hormone." J. of Investig. Med. 45 (5):276-283, 1997.
Hasegawa et al. "Identification of a binding region on *Escherichia coli* heat-stable enterotoxin to intestinal guanylyl cyclase C," Letters in Peptide Sci., 4, pp. 1-11, 1997.
Heck et al., "Modification and inhibition of vancomycin group antibiotics by formaldehyde and acetaldehyde." Chemistry—A European Journal 7, No. 4: 910-916, 2001.
Hepner et al., "Mass spectrometrical analysis of recombinant human growth hormone (Genotropin®) reveals amino acid substitutions in 2% of the expressed protein." Proteome Science, 3:1, 1-12, 2005.
Hirayama et al., "Heat-stable enterotoxin of *Escherichia coli*." In Bacterial Protein Toxins, pp. 577-593. Springer, Berlin, Heidelberg, 2000.
Ikemura et al., "Heat-stable enterotoxin (STh) of human enterotoxigenic *Escherichia coli* (strain Sk-1). Structure-activity Relationship." Bulletin of the Chemical Society of Japan 57, No. 9: 2550-2556, 1984.
International Council for Harmonisation of Technical Requirements for Pharmaceuticals for Human Use (ICH), "Dose-Response Information to Support Drug Registration". ICH-E4, 1994.
Jacob et al., "The sulfinic acid switch in proteins." Organic & biomolecular chemistry 2, No. 14: 1953-1956, 2004.
Kyaw et al., "Intracellular Distribution of Radio-labelled Enterotoxigenic *Escherichia coli* Heat-Stable Toxin (STa) in the Intestine of Suckling Rat." Journal of Diarrhoeal Diseases Research: 232-234, 1995.
Lacy, "ACG 2006—Evaluation and Treatment of IBS and Chronic Constipation". Medscape Gastoenterology, available from Medscape. com, 2006.
Ladunga et al., "Amino acid substitutions preserve protein folding by conserving steno and hydrophobicity properties." Protein Engineering, 10(3): 187-196, 1997.
Li et al., "Detection and quantification of low-molecular-weight aldehydes in pharmaceutical excipients by headspace gas chromatography." Journal of Chromatography A 1104.1-2, pp. 1-10, 2006.
Lloyd-Williams et al., "Chemical approaches to the synthesis of peptides and proteins". Chapters 2 and 5, Boca Raton, CRC Press, 1997.
Mandake et al., "Kinetic study of catalyzed and uncatalyzed esterification reaction of acetic acid with methanol." American International Journal of Research in Science, Technology, Engineering & Mathematics 3, No. 1: 114-121, 2013.
Manning et al., "Stability of protein pharmaceuticals." Pharmaceutical research, 6(11), pp. 903-918, 1989.
Martinus et al., "High throughput screening of protein formulation stability: Practical considerations". European Journal of Pharmaceutics and Biopharmaceutics, vol. 65, Issue 2, pp. 131-148, Feb. 2007.
Metz et al.: "Identification of Formaldehyde-induced Modifications in Proteins—Reactions with Model Peptides." Journal of Biological Chemistry, 279: 6235-6243, 2004.
Mezoff et al., "*Escherichia coli* enterotoxin (STa) binds to receptors, stimulates guanyl cyclase, and impairs absorption in rat colon." Gastroenterology 102, No. 3: 816-822, 1992.
Microbia, "Linclotide Shown to Improve Symptoms of Chronic Constipation in Phase 2A Study." Press release published on Oct. 24, 2006.
Microbia, "Microbia Announces Positive Phase 2 Results for its Investigational Compound Linaclotide." Press release published on May 21, 2007.
Moss et al., Handbook of Natural Toxins: Bacterial Toxins and Virulence Factors in Disease, vol. 8, CRC Press, 664 pages, Mar. 21, 1995.
Nakazato, "Guanylin family: new intestinal peptides regulating electrolyte and water homeostasis." Journal of gastroenterology 36, No. 4: 219-225, 2001.
Nicolaou, et al., "Taxoids: new weapons against cancer." Scientific American 274, No. 6 (1996): 94-98.
Niu et al., "FDA perspective on peptide formulation and stability issues." Journal of pharmaceutical sciences 87, No. 11: 1331-1334, 1998.
Oliyai et al., "Prodrugs of peptides and proteins for improved formulation and delivery." Annu. Rev. Pharmacol. Toxicol., 32:521-544, 1993.
Rasmussen et al., "Prodrugs of peptides. 10. Protection of di-and tripeptides against aminopeptidase by formation of bioreversible 4-imidazolidinone derivatives." International journal of pharmaceutics 71, No. 1-2: 45-53, 1991.
Roussel et al., "Myoelectric activity of the small intestine in enterotoxin-induced diarrhea of calves." American journal of veterinary research 53, No. 7: 1145-1148, 1992.
Sack, "Enterotoxigenic *Escherichia coli*: identification and characterization." The Journal of infectious diseases 142, No. 2: 279-286, 1980.
Schiller, "The therapy of constipation." Alimentary pharmacology & therapeutics 15, No. 6: 749-763, 2001.
Schmidt, "Dose-finding studies in clinical drug development." European journal of clinical pharmacology 34, No. 1: 15-19, 1988.
Shailubhai, K., "Therapeutic Applications of Guanylate Cyclase-C Receptor Agonists", Current Opinion in Drug Discovery and Development, 5(2):261-268, Mar. 2002.
Shimonishi et al., "Mode of Disulfide Bond Formation of a Heat-Stable Enterotoxin (STh) Produced by a Human Strain of Enterotoxigenic *Escherichia coli*." FEBS, 215(1):165-170, 1987.
Silberstein, et al., "Botulinum toxin type A as a migraine preventive treatment." Headache: The Journal of Head and Face Pain 40, No. 6: 445-450, 2000.
Son et al., "Stabilization of human epidermal growth factor (hEGF) in aqueous formulation." Pharmaceutical research 12, No. 3: 451-454, 1995.
Stryer, "Biochemistry." New York: W.H. Freeman, 1988.
Tabb et al., "Characterization of a p-azidophenylalanine as a system L substrate and a photoaffinity probe." Fed. Am. Soc. Exp. Biol. 45(6):Conference 6, 1986 (Abstract only).
Tajima,et al., "Role of calcium ions in the thermostability of thermolysin and *Bacillus subtilis* var. *amylosacchariticus* neutral protease." European journal of biochemistry 64, No. 1: 243-247, 1976.
Troy et al., Remington. "The Science and Practice of Pharmacy". Lippincott Williams & Wilkins, 21st Ed., 2006.
U.S. Pharmacopoeia and the National Formulary, USP 23-NF18, 1995.

(56) References Cited

OTHER PUBLICATIONS

Van Den Eijnden et al., "Disulfide bonds determine growth hormone receptor folding, dimerisation and ligand binding." Journal of cell science 119, No. 15: 3078-3086, 2006.
Volkin et al., "Degradative covalent reactions important to protein stability." Molecular biotechnology 8, No. 2: 105-122, 1997.
Wolfe and Waldman, "A Comparative Molecular Field Analysis (COMFA) of the Structural Determinants of Heat-Stable Enterotoxins Mediating Activation of Guanylyl Cyclase C." J. Med. Chem. 45:1731-1734, 2002.
Wu et al., "Reactive impurities in excipients: profiling, identification and mitigation of drug—excipient incompatibility." AAPS PharmSciTech 12, No. 4: 1248-1263, 2011.
Yoshimura et al., "Essential structure for full enterotoxigenic activity of heat-stable enterotoxin produced by enterotoxigenic *Escherichia coli*," FEBS Letters, 181(1), pp. 138-142, 1985.
Ahmed, Hashim and Shah, Navnit., "Formulations of Low Dose Medicines—Theory and Practice." American Pharmaceutical Review, 3(3): 1-4, 2000.
Andresen et al., "Effect of 5 days of linaclotide on transit and bowel function in females with constipation-predominant irritable bowel syndrome." Gastroenterology, 133(3):761-768, 2007.
Andresen et al., "Linaclotide Acetate." Drugs of the Future, 33(7): 570-576, 2008.
Aventis Pharmaceuticals, Inc. (2002). DDAVP (desmopressin acetate) tablet, [Product Label]. Bridgewater, NJ 08807, USA.
Bedu-Addo, F. et al., "Preformulation Development of Recombinant Pegylated Staphylokinase SY161 Using Statistical Design." AAPS PharmSci (http://www.aapspharmsci.org), 4(4) article 19, 1-11, 2002.
Bedu-Addo, F.K. et al., "Use of Biophysical Characterization in Preformulation Development of a Heavy-Chain Fragment of Botulinum Serotype B: Evaluation of Suitable Purification Process Conditions." Pharmaceutical Research, 21(8): 1353-1361, 2004.
Camilleri, "Management of the Irritable Bowel Syndrome" Gastroenterology, 120:652-668, 2001.
Capasso et al., "Deamidation via Cyclic Imide of Asparaginyl Peptides: Dependence on Salts, Buffers and Organic Solvents." Peptide Research, 4(4): 234-238, 1991.
Carpenter et al., "Rational Design of Stable Lyophilized Protein Formulations: Some Practical Advice." Pharmaceutical Research, 14(8): 969-975, 1997.
Chourasia, M.K. and Jain, S.K., "Pharmaceutical approaches to colon targeted drug delivery systems." J Pharm Pharmaceut Sci (www.ualberta.ca/-csps), 6(1): 33-66, 2003.
Cleland et al., "The Development of Stable Protein Formulations: A Close Look at Protein Aggregation, Deamidation, and Oxidation." Critical Reviews in Therapeutic Drug Carrier Systems, 10(4): 307-377, 1993.
Constantino, H.R, et al., "Moisture-Induced Aggregation of Lyophilized Insulin". Pharmaceutical Research, 11(1): 21-29, 1994.
Cook et al., "Chronic constipation: Overview and Challenges." Neurogastroenterology and Motility, 21(supp2): 1-8, 2009.
Dulbecco et al., "Plaque formation and isolation of pure liner with poliomyelitis viruses." Journal of Experimental Medicine, 99(2): 167-182, 1954.
Elan Pharmaceuticals, Inc. (2004). PRIALT (ziconotide) injection, solution, [Product Label]. San Diego, CA 92121, USA.
Fix, J.A., "Oral Controlled Release Technology for Peptides: Status and Future Prospects." Pharmaceutical Research, 13(12): 1760-1764, 1996.
Forest, "Phase III randomized double-blind placebo-controlled trial of linaclotide administered to patients with chronic constipation." 2008. Retrieved from «http:www.clinicaltrials.gov» identifier NCT00765882 on Dec. 9, 2010.
Fu et al., "Protein Stability in Controlled-Release Systems." Nature Biotechnology, 18: 24-25, 2000.
Fujita et al. "Stabilization by meglumine of an amine compound degraded by formaldehyde in tablets." International journal of pharmaceutics 386.1-2: 195-200, 2010.
Grenha et al., "Chitosan nanoparticles are compatible with respiratory epithelial cells in vitro." European Journal of Pharmaceutical Sciences, 31: 73-84, 2007.
Harris et al., "Drug evaluation: Linaclotide, a new direction in the treatment of irritable bowel syndrome and chronic constipation." Current Opinion in Molecular Therapeutics, 9(4):403-410, 2007.
Harris, "Constipation: Linaclotide—a stimulating new drug for chronic constipation." Nature Reviews Gastroenterology and Hepatology, 7(7):365-6, 2010.
"International Nonproprietary Names for Pharmaceutical Substances (INN)." WHO Drug Information, 21(3): 247-264, 2007.
Johnston et al., "Pilot study on the effect of linaclotide in patients with chronic constipation." Am. J. Gastroenterol., 104(1):125-132, 2009.
Kirby, "Oil-Based Formulations for Oral Delivery of Therapeutic Peptides." Journal of Liposome Research, 10(4): 391-407, 2000.
Langer, R. "Drug delivery and targeting", Nature; 392 (Supp): 5-10, 1998.
Lavins et al., "418 Effect of Linaclotide on Quality of Life in Adults with Chronic Constipation: Results from a Phase 2B Study." Gastroenterology, 136(5): A71, 2009.
Lechuga-Ballesteros et al., "Trileucine Improves Aerosol Performance and Stability of Spray-dried Powders for Inhalation." Journal of Pharmaceutical Sciences, 97(1): 287-302, 2008.
Lembo et al., "Linaclotide significantly improved bowel habits and relieved abdominal symptoms in adults with chronic constipation: Data from a large 4-week, randomized, double-blind, placebo-controlled study." Gastroenterology, 135 (1):295, 2008.
Lembo et al., "157 Effect of Linaclotide on IBS-C Symptoms in the First Week of Treatment: Results from a Phase 2B Study" . Gastroenterology, 136(5):A30, 2009.
Mehta, N.M., "Oral Delivery and Recombinant Production of Peptide Hormones. Part I: Making Oral Delivery Possible: Enteric-coated capsules or tablets with additional excipients enable intestinal delivery." Bio-Pharm International (www.biopharm-mag.com), Jun. 1-6, 2004.
Mehta, N.M., "Oral Delivery and Recombinant Production of Peptide Hormones. Part II: Recombinant Production of Therapeutic Peptides." Bio-Pharm International (www.biopharm-mag.com), Jun. 7-9, 2004.
Microbia, Forest, "Microbia and Forest Laboratories Announce Preliminary Results of Linaclotide Phase 2B Studies." Communications of Microbia, pp. 1-4, 2008.
Oliyai et al., "Chemical Pathways of Peptide Degradation. VII. Solid State Chemical Instability of an Aspartyl Residue in a Model Hexapeptide." Pharmaceutical Research, 11(6): 901-908, 1994.
Oliyai et al., "Solid State Chemical Instability of an Asparaginyl Residue in a Model Hexapeptide." Journal of Pharmaceutical Science & Technology, 48(3): 167-173, 1994.
Patel, K. and Borchardt, R.T., "Chemical Pathways of Peptide Degradation. III. Effect of Primary Sequence on the Pathways of Deamidation of Asparaginyl Residues in Hexapeptides." Pharmaceutical Research, 7(8): 787-793, 1990.
Patel, K. and Borchardt, R.T., "Deamidation of Asparaginyl Residues in Proteins: A Potential Pathway for Chemical Degradation of Proteins in Lyophilized Dosage Forms." Journal of Parenteral Science & Technology, 44(6): 300-301, 1990.
Patel et al., "Activated ketone based inhibitors of human renin." Journal of Medicinal Chemistry, 36(17):2431-47, 1993.
Reporter's Guide to Irritable Bowel Syndrome, retrieved from «http:www.aboutibs.org/pdfs/ReportersGuideIBS.pdf» on Nov. 28, 2012, total of 18 pages where the main text is numbered as pp. 1-14.
Sejourne, F. et al., "Development of a Novel Bioactive Formulation of Vasoactive Intestinal Peptide in Sterically Stabilized Liposomes." Pharmaceutical Research, 14(3): 362-365, 1997.
Shailubhai et al., "Uroguanylin treatment suppresses polyp formation in the Apc(Min/+) mouse and induces apoptosis in human colon adenocarcinoma cells via cyclic GMP." Cancer Res., 60:5151-5157, 2000.
Vippagunta et al., "Crystalline solids." Advanced Drug Delivery Reviews, 48:3-26, 2001.

(56) References Cited

OTHER PUBLICATIONS

Angelastro et al., "An efficient synthesis of novel alpha-diketone and alpha-keto ester derivatives of N-protected amino acids and peptides." The Journal of Organic Chemistry, 54(16):3913-6, 1989.
Camilleri et al., "Challenges to the Therapeutic Pipeline for Irritable Bowel Syndrome: End Points and Regulatory Hurdles." Gastroenterology. 135:1877-1891, 2008.
Carson et al.,"Effect of Linaclotide on Quality of Life in Adults With Chronic Constipation: Results From 2 Randomized, Double-Blind, Placebo-Controlled Phase III Trials." Gastroenterology, 139(1):E19, 2010.
Capelle et al., "High throughput screening of protein formulation stability: practical considerations." European journal of pharmaceutics and biopharmaceutics, 65(2): 131-148, 2007.
Gliński et al., "Surface properties of aqueous solutions of L-leucine." Biophysical Chemistry, 84(2): 99-103, 2000.
Learoyd et al., "Chitosan-based spray-dried respirable powders for sustained delivery of terbutaline sulfate." European journal of pharmaceutics and biopharmaceutics, 68(2): 224-234, 2008.
Matubayasi et al., "Thermodynamic quantities of surface formation of aqueous electrolyte solutions: V. Aqueous solutions of aliphatic amino acids." Journal of colloid and interface science, 250(2): 431-437, 2002.
Motheram, "Behavior of recombinant human growth hormone at solid/liquid interfaces." Doctoroal dissertation, University of the Sciences in Philadelphia, 2007.
Ozaki et al., "Molecular structure of the toxin domain of heat-stable enterotoxin produced by a pathogenic strain of *Escherichia coli*. A putative binding site for a binding protein on rat intestinal epithelial cell membranes." Journal of Biological Chemistry, 266(9): 5934-5941, 1991.
Raula et al., "Study of the dispersion behaviour of L-leucine containing microparticles synthesized with an aerosol flow reactor method." Powder Technology, 177(3): 125-132, 2007.
Sato et al., "Structural characteristics for biological activity of heat-stable enterotoxin produced by enterotoxigenic *Escherichia coli*: X-ray crystallography of weakly toxic and nontoxic analogs." Biochemistry, 33(29): 8641-8650, 1994.
Szenczi et al., "The effect of solvent environment on the conformation and stability of human polyclonal IgG in solution." Biologicals, 34(1): 5-14, 2006.
Difeo, T.J., "Drug product development: a technical review of chemistry, manufacturing, and controls information for the support of pharmaceutical compound licensing activities." Drug development and industrial pharmacy 29, No. 9: 939-958, 2003.
Greibenow et al., "Lyophilization-induced reversible changes in the secondary structure of proteins." Proceedings of the National Academy of Sciences 92, No. 24: 10969-10976, 1995.
Hu et al., "β—Sheet structure formation of proteins in solid state as revealed by circular dichroism spectroscopy." Biopolymers: Original Research on Biomolecules 62, No. 1: 15-21, 2001.
Nozaki et al., "The solubility of amino acids and two glycine peptides in aqueous ethanol and dioxane solutions establishment of a hydrophobicity scale." Journal of Biological Chemistry 246, no. 7: 2211-2217, 1971.
Pearlman et al., "Formulation strategies for recombinant proteins: Human growth hormone and tissue plasminogen activator." Therapeutic peptides and proteins: Formulations, delivery, and targeting. Cold Spring Harbor, NY: Current Communications in Molecular Biology: 23-30, 1989.
Shiraki et al., "Biophysical effect of amino acids on the prevention of protein aggregation." The Journal of Biochemistry 132, No. 4: 591-595, 2002.

* cited by examiner

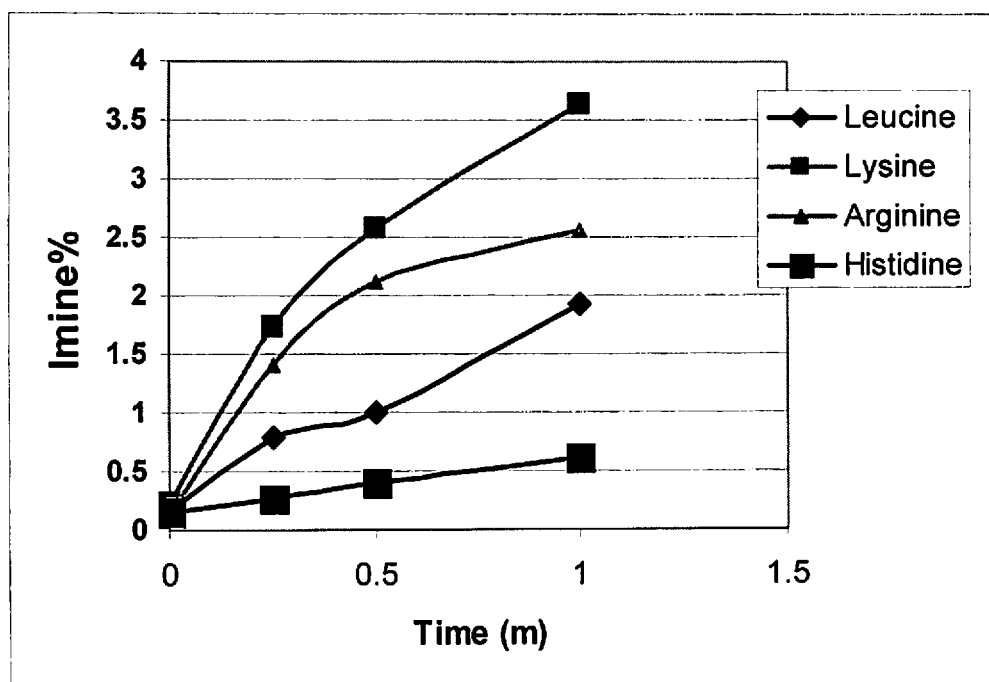

STABLE FORMULATIONS OF LINACLOTIDE

CLAIM OF PRIORITY

This application is a continuation of U.S. patent application Ser. No. 16/006,070 filed Jun. 12, 2018, which is the continuation of U.S. patent application Ser. No. 15/727,700 filed Oct. 9, 2017, which is the continuation of U.S. patent application Ser. No. 15/439,049 filed Feb. 22, 2017, which is the continuation of U.S. patent application Ser. No. 15/203,951 filed Jul. 7, 2016, which is the continuation of U.S. patent application Ser. No. 14/948,795 filed Nov. 23, 2015, which is the continuation of U.S. patent application Ser. No. 14/689,561 filed Apr. 17, 2015, which is the continuation of U.S. patent application Ser. No. 14/484,568 filed Sep. 12, 2014, which is the continuation of U.S. patent application Ser. No. 13/816,154 filed Feb. 8, 2013, which is the United States national phase application of PCT/US2011/047434, filed on Aug. 8, 2011. This application also claims priority to U.S. Provisional Patent Application Ser. No. 61/372,804 filed Aug. 8, 2010. The entire contents of the aforementioned applications are incorporated herein by reference.

SEQUENCE LISTING

This application incorporates by reference in its entirety the Sequence Listing entitled "IW099PCT11CON8a_T25.txt" which is 3.24 kilobytes in size and last modified on Mar. 27, 2020 and filed electronically herewith.

FIELD OF THE INVENTION

The present invention relates to stable pharmaceutical compositions of linaclotide and methods for treating gastrointestinal disorders (e.g., irritable bowel syndrome or chronic constipation) by administering the pharmaceutical compositions.

BACKGROUND OF THE INVENTION

Linaclotide is a peptide that is useful as an agonist of the guanylate cyclase C (GC-C) receptor in the treatment of gastrointestinal disorders. Linaclotide is described, for example, in U.S. Pat. Nos. 7,304,036 and 7,371,727, the contents of which are incorporated herein by reference in their entirety.

There is an existing and continual need for linaclotide formulations, for example, low-dose and pediatric formulations, having improved stability and performance. This need arises in part because of the intrinsic and chemical instability of linaclotide (for example, induced by moisture-driven degradation reactions such as hydrolysis, deamidation, isomerization, and multimerization). These difficulties may be exacerbated when producing pediatric formulations and other low-dose formulations of linaclotide, e.g., because the linaclotide is more dispersed and has greater surface area exposure to aqueous environments such as during preparation.

The present invention provides such improved stability formulations of linaclotide. These formulations are described herein.

BRIEF DESCRIPTION OF THE FIGURES

FIG. 1 illustrates stability performance data for the linaclotide compositions prepared in Examples 2-5 as described in Example 6.

SUMMARY OF THE INVENTION

In some embodiments of the present invention, a stable pharmaceutical composition is provided which comprises linaclotide, a cation or salt thereof, and a sterically hindered amine selected from meglumine, histidine or a mixture thereof, and, optionally, a polymer.

In some embodiments, the pharmaceutical composition comprises linaclotide, a cation or pharmaceutically acceptable salt thereof and an amine selected from meglumine or a mixture of meglumine and histidine.

In some embodiments, the pharmaceutical composition comprises linaclotide, a cation or pharmaceutically acceptable salt thereof and histidine, wherein the composition has a molar ratio of cation:histidine of less than 2:1.

In some embodiments, a stable pharmaceutical composition is provided which comprises linaclotide, a cation or salt thereof, meglumine, and, optionally, a polymer.

In some embodiments, a stable pharmaceutical composition is provided which comprises linaclotide, a cation or salt thereof, histidine, and, optionally, a polymer.

In some embodiments, the pharmaceutical composition further comprises a polymer.

In some embodiments, a pharmaceutical composition (e.g., capsule, tablet, granule or bead) is provided which comprises linaclotide, a cation or pharmaceutically acceptable salt thereof, a sterically hindered amine selected from histidine, meglumine or a mixture thereof, and a polymer selected from polyvinyl pyrrolidone (PVP), polyvinyl alcohol (PVA) or a mixture thereof.

In some embodiments, a pharmaceutical composition is provided which comprises linaclotide, a cation or pharmaceutically acceptable salt thereof, and melamine. In some embodiments, the pharmaceutical composition further comprises a polymer.

In some embodiments, a pharmaceutical composition is provided which comprises linaclotide, a cation or pharmaceutically acceptable salt thereof, and gelatin. In some embodiments, the pharmaceutical composition further comprises a polymer.

In some embodiments, a pharmaceutical composition is provided which comprises linaclotide, a cation or pharmaceutically acceptable salt thereof, and glycine. In some embodiments, the pharmaceutical composition further comprises a polymer.

In some embodiments, a pharmaceutical composition is provided which comprises linaclotide, a cation or pharmaceutically acceptable salt thereof, and the dipeptide glycine-leucine.

In some embodiments, the pharmaceutical composition further comprises a polymer.

In some embodiments, a pharmaceutical composition is provided which comprises linaclotide, a cation or pharmaceutically acceptable salt thereof, and the dipeptide leucine-glycine.

In some embodiments, the pharmaceutical composition further comprises a polymer.

In some embodiments, a pharmaceutical composition is provided which comprises linaclotide, a cation or pharmaceutically acceptable salt thereof, and albumin. In some embodiments, the pharmaceutical composition further comprises a polymer.

In some embodiments, a pharmaceutical composition is provided which comprises linaclotide, a cation or pharmaceutically acceptable salt thereof, and asparagine. In some embodiments, the pharmaceutical composition further comprises a polymer.

In some embodiments, a stable low-dose pharmaceutical composition of linaclotide is provided. In some embodiments, a stable pediatric pharmaceutical composition of linaclotide is provided.

In some embodiments, a method of treating a gastrointestinal disorder comprising administering to a patient in need thereof, a therapeutically effective amount of the pharmaceutical compositions described above.

DETAILED DESCRIPTION OF THE INVENTION

Stable formulations of linaclotide (SEQ ID NO: 1) are provided herein. In addition, methods of using the formulations to treat gastrointestinal disorders, including irritable bowel syndrome ("IBS") (for example, constipation-predominant IBS) and/or constipation (for example, chronic constipation), and processes for making the compositions are provided.

It has been found that the stability of linaclotide within solid oral dosage forms (e.g., capsules and tablets) can be improved by combining linaclotide with specific concentrations or molar ratios of a cation or pharmaceutically acceptable salt thereof, and an amine selected from histidine, meglumine or combination thereof. In some embodiments, stability may be improved by combining linaclotide with specific concentrations or molar ratios of a polymer, cation or pharmaceutically acceptable salt thereof, and an amine selected from histidine, meglumine or combination thereof. It has been found, in some embodiments, that combining these components with linaclotide causes a synergistic increase or improvement in the stability of linaclotide within the composition, for example as compared to similar compositions not containing the cation and/or sterically hindered amine and/or the same concentrations of these components.

The pharmaceutical composition may include any effective amount of linaclotide. In some embodiments, for example, the composition comprises from 0.001 μg to 400 μg of linaclotide. In some embodiments, for example, the composition comprises from 0.001 μg to 350 μg of linaclotide. In some embodiments, for example, the composition comprises from 0.001 μg to 300 μg of linaclotide. In some embodiments, for example, the composition comprises from 0.001 μg to 250 μg of linaclotide. In some embodiments, for example, the composition comprises from 0.001 μg to 200 μg of linaclotide. In some embodiments, for example, the composition comprises from 0.001 μg to 150 μg of linaclotide. In some embodiments, for example, the composition comprises from 0.001 μg to 125 μg of linaclotide. In some embodiments, for example, the composition comprises from 0.001 μg to 100 μg of linaclotide. In some embodiments, for example, the composition comprises from 0.001 μg to 80 μg of linaclotide. In some embodiments, for example, the composition comprises from 0.001 μg to 60 μg of linaclotide. In some embodiments, for example, the composition comprises from 0.001 μg to 50 μg of linaclotide. In some embodiments, for example, the composition comprises from 0.001 μg to 40 μg of linaclotide. In some embodiments, for example, the composition comprises from 0.001 μg to 30 μg of linaclotide.

In some embodiments, the composition comprises 0.001 μg to 300 μg of linaclotide (e.g., 0.01 μg to 300 μg, 0.1 μg to 300 μg, 1 μg to 300 μg, 5 μg to 300 μg, 10 μg to 300 μg, 25 μg to 300 μg, or 50 μg to 300 μg of linaclotide). In some embodiments, the composition comprises 0.001 μg to 200 μg of linaclotide (e.g., 0.01 μg to 200 μg, 0.1 μg to 200 μg, 1 μg to 200 μg, 5 μg to 200 μg, 10 μg to 200 μg, 25 μg to 200 μg, or 50 μg to 200 μg of linaclotide). In some embodiments, the composition comprises 0.001 μg to 125 μg of linaclotide (e.g., 0.01 μg to 125 μg, 0.1 μg to 125 μg, 1 μg to 125 μg, 5 μg to 125 μg, 10 μg to 125 μg, 25 μg to 125 μg, or 50 μg to 125 μg of linaclotide). In some embodiments, the composition comprises 0.01 μg to 100 μg of linaclotide (e.g., 0.1 μg to 100 μg, 1 μg to 100 μg, 5 μg to 100 μg, 10 μg to 100 μg, 25 μg to 100 μg, or 50 μg to 100 μg of linaclotide). In some embodiments, the composition comprises 0.01 μg to 75 μg of linaclotide (e.g., 0.1 μg to 75 μg, 1 μg to 75 μg, 5 μg to 75 μg, 10 μg to 75 μg, 25 μg to 75 μg, or 50 μg to 75 μg of linaclotide). In some embodiments, the composition comprises 0.01 μg to 50 μg of linaclotide (e.g., 0.1 μg to 50 μg, 1 μg to 50 μg, 5 μg to 50 μg, 10 μg to 50 μg, or 20 μg to 50 μg of linaclotide).

In some embodiments, the composition comprises 0.001 μg, 0.005 μg, 0.01 μg, 0.05 μg, 0.1 μg, 0.15 μg, 0.25 μg, 0.5 μg, 0.75 μg, 1 μg, 2.5 μg, 5 μg, 7.5 μg, 10 μg, 20 μg, 30 μg, 40 μg, 50 pig, 60 μg, 80 μg, 100 μg, 125 μg, 133 μg, 150 μg, 200 μg, 250 μg, 266 μg, 300 μg, 350 μg, 400 μg, 450 μg, 500 μg, 550 μg, 600 μg, 650 μg, 700 μg, 750 μg, 800 μg, 850 μg, 900 μg, 950 μg or 1 mg of linaclotide. In some embodiments, the composition comprises 75 μg of linaclotide. In some embodiments, the composition comprises 133 μg of linaclotide. In some embodiments, the composition comprises 150 μg of linaclotide. In some embodiments, the composition comprises 266 μg of linaclotide. In some embodiments, the composition comprises 300 μg of linaclotide. In some embodiments, the composition comprises 600 μg of linaclotide.

In some embodiments, the pharmaceutical composition (e.g., bead or granule) comprises 0.00001 to 5% by weight of linaclotide, for example, 0.00001 to 3% by weight, 0.00001 to 1% by weight, 0.0001 to 0.5% by weight, 0.0001 to 0.3% by weight, 0.0001 to 0.1% by weight, 0.0001 to 0.07 wt. %, 0.0005 to 0.05 wt. %, 0.005 to 0.04 wt. %, 0.008 to 0.03 wt. %, 0.008 to 0.02 wt. %, 0.008 to 0.015 wt. %, or about 0.012% by weight of linaclotide.

In some embodiments, the pharmaceutical composition also comprises meglumine, histidine or a combination or mixture thereof. In some embodiments, the pharmaceutical composition comprises linaclotide, a cation or pharmaceutically acceptable salt thereof and an amine selected from meglumine or a mixture of meglumine and histidine. In other embodiments, the pharmaceutical composition comprises linaclotide, a cation or pharmaceutically acceptable salt thereof and histidine, wherein the composition has a molar ratio of cation:histidine of less than 2:1. For example, in some embodiments, the pharmaceutical composition comprises meglumine. In some embodiments, the pharmaceutical composition comprises histidine. In some embodiments, the pharmaceutical composition comprises meglumine and histidine.

The pharmaceutical composition can comprise any stabilizing amount of meglumine, histidine or mixture thereof. In some embodiments, for example, the composition comprises a molar ratio of meglumine, histidine (or mixture thereof) to linaclotide between 100:1 and 1:100. In some embodiments, the composition comprises a molar ratio of meglumine, histidine (or mixture thereof) to linaclotide between 100:1 and 1:1. In some embodiments, the composition comprises a molar ratio of meglumine, histidine (or mixture thereof) to linaclotide between 90:1 and 2:1. In some embodiments, the composition comprises a molar ratio of meglumine, histidine (or mixture thereof) to linaclotide between 80:1 and 5:1. In some embodiments, the composition comprises a molar ratio of meglumine, histidine (or mixture thereof) to linaclotide between 70:1 and 10:1. In some embodiments, the composition comprises a molar ratio of meglumine, histidine (or mixture thereof) to linaclotide between 60:1 and 20:1. In some embodiments, the composition comprises a molar ratio of meglumine, histidine (or mixture thereof) to linaclotide between 50:1 and 30:1. In some embodiments, the composition comprises a molar ratio of meglumine, histidine (or mixture thereof) to linaclotide between 40:1 and 20:1. In some embodiments, the composition comprises a molar ratio of meglumine, histidine (or mixture thereof) to linaclotide between 100:1 and 20:1. In some embodiments, the composition comprises a molar ratio of meglumine, histidine (or mixture thereof) to linaclotide between 100:1 and 25:1.

In some embodiments, the composition comprises a molar ratio of meglumine, histidine (or mixture thereof) to linaclotide between 100:1 and 30:1. In some embodiments, the composition comprises a molar ratio of meglumine, histidine (or mixture thereof) to linaclotide between 100:1 and 40:1. In some embodiments, the composition comprises a molar ratio of meglumine, histidine (or mixture thereof) to linaclotide between 100:1 and 50:1. In some embodiments, the composition comprises a molar ratio of meglumine, histidine (or mixture thereof) to linaclotide between 100:1 and 60:1. In some embodiments, the composition comprises a molar ratio of meglumine, histidine (or mixture thereof) to linaclotide between 100:1 and 70:1. In some embodiments, the composition comprises a molar ratio of meglumine, histidine (or mixture thereof) to linaclotide of at least 5:1. In some embodiments, the composition comprises a molar ratio of meglumine, histidine (or mixture thereof) to linaclotide of at least 10:1. In some embodiments, the composition comprises a molar ratio of meglumine, histidine (or mixture thereof) to linaclotide of at least 20:1. In some embodiments, the composition comprises a molar ratio of meglumine, histidine (or mixture thereof) to linaclotide of at least 25:1. In some embodiments, the composition comprises a molar ratio of meglumine, histidine (or mixture thereof) to linaclotide of at least 30:1. In some embodiments, the composition comprises a molar ratio of meglumine, histidine (or mixture thereof) to linaclotide of at least 40:1.

In some embodiments, the pharmaceutical composition (e.g., capsule, tablet, bead or granule) comprises a molar ratio of meglumine, histidine (or mixture thereof) (e.g., an amine such as histidine or meglumine) to linaclotide between 200:1 and 1:1. In some embodiments, the composition comprises a molar ratio of meglumine, histidine (or mixture thereof) to linaclotide between 175:1 and 10:1. In some embodiments, the composition comprises a molar ratio of meglumine, histidine (or mixture thereof) to linaclotide between 160:1 and 30:1. In some embodiments, the composition comprises a molar ratio of meglumine, histidine (or mixture thereof) to linaclotide between 150:1 and 50:1. In some embodiments, the composition comprises a molar ratio of meglumine, histidine (or mixture thereof) to linaclotide between 125:1 and 75:1. In some embodiments, the composition comprises a molar ratio of meglumine, histidine (or mixture thereof) to linaclotide between 120:1 and 80:1. In some embodiments, the composition comprises a molar ratio of meglumine, histidine (or mixture thereof) to linaclotide between 110:1 and 90:1.

In some embodiments, the composition (e.g., bead) comprises 0.00001 to 1% by weight of histidine. In some embodiments, the composition comprises 0.0001 to 0.5% by weight of histidine. In some embodiments, the composition comprises 0.0001 to 0.3% by weight of histidine (for example, 0.0001 to 0.1% by weight, 0.001 to 0.07 wt. %, 0.005 to 0.05 wt. %, 0.005 to 0.04 wt. %, 0.008 to 0.03 wt. %, 0.008 to 0.02 wt. %, 0.008 to 0.015 wt. %, 0.008 to 0.012 wt. %, or even about 0.01% by weight of histidine).

In some embodiments, the composition (e.g., bead or granule) comprises 0.00001 to 1% by weight of meglumine. In some embodiments, the composition comprises 0.0001 to 0.5% by weight of meglumine. In some embodiments, the composition comprises 0.0001 to 0.3% by weight of meglumine (for example, 0.0001 to 0.1% by weight, 0.001 to 0.07 wt. %, 0.005 to 0.05 wt. %, 0.005 to 0.04 wt. %, 0.008 to 0.03 wt. %, 0.008 to 0.02 wt. %, 0.008 to 0.015 wt. %, 0.008 to 0.012 wt. %, or even about 0.01% by weight of meglumine).

In some embodiments, the pharmaceutical composition comprises melamine, gelatin, glycine, glycine-leucine, albumin or asparagine in place of, or in combination with, the meglumine, histidine (or mixture thereof) component. The melamine, gelatin, glycine, glycine-leucine, albumin or asparagine can be included in the composition in any desired amount, such as at the same concentration or in the same molar ratios disclosed herein with respect to the meglumine and histidine component.

The pharmaceutical composition can comprise any suitable cation(s) or pharmaceutically acceptable salt thereof. Suitable cations include, for example, metal or organic cations. In some embodiments, the composition comprises a metal cation selected from calcium, potassium, magnesium, zinc, aluminum, iron, tin, manganese, chromium, cobalt, nickel, barium, sodium, or a combination or mixture thereof. In some embodiments, the composition comprises a metal cation selected from calcium, potassium, magnesium, zinc, aluminum, manganese, chromium, cobalt, nickel, barium, sodium, or a combination or mixture thereof. In some embodiments, the composition comprises a metal cation selected from aluminum, calcium, potassium, sodium, magnesium, manganese, zinc, or a combination or mixture thereof. In some embodiments, the composition comprises a metal cation selected from calcium, magnesium, manganese, zinc, or a combination or mixture thereof. In some embodiments, the composition comprises a divalent metal cation. In some embodiments, the composition comprises a divalent metal cation selected from $Ca^{2+}$, $Mg^{2+}$, $Zn^{2+}$, $Mn^{2+}$, or a combination or mixture thereof. In some embodiments, the composition comprises $Mg^{2+}$. In some embodiments, the composition comprises $Ca^{2+}$. In some embodiments, the composition comprises $Zn^{2+}$. In some embodiments, the composition comprises aluminum.

The cation can be added to the composition in any suitable form, for example any pharmaceutically acceptable salt with any appropriate counterion. Suitable metal salts include, for example, calcium chloride, calcium carbonate, calcium acetate, magnesium chloride, magnesium acetate, zinc acetate, zinc chloride, aluminum chloride or mixtures thereof. In some embodiments, the composition comprises calcium chloride, magnesium chloride, zinc acetate, or a combination or mixture thereof. In some embodiments, the composition comprises calcium chloride. In some embodiments, the composition comprises magnesium chloride. In some embodiments, the composition comprises zinc acetate.

Suitable organic cations include, for example, ammonium hydroxide, D-arginine, L-arginine, t-butylamine, calcium acetate hydrate, calcium carbonate, calcium DL-malate, calcium hydroxide, choline, ethanolamine, ethylenediamine, glycine, L-histidine, L-lysine, magnesium hydroxide, N-methyl-D-glucamine, L-ornithine hydrochloride, potassium hydroxide, procaine hydrochloride, L-proline, pyridoxine, L-serine, sodium hydroxide, DL-tryptophan, tromethamine, L-tyrosine, L-valine, carnitine, taurine, creatine malate, arginine alpha keto glutarate, ornithine alpha keto glutarate, spermine acetate, spermidine chloride, or combinations or mixtures thereof. In some embodiments, the organic cation is selected from the group consisting of N-methyl D-glucamine, choline, arginine, lysine, procaine, tromethamine (TRIS), spermine, N-methyl-morpholine, glucosamine, N,N-bis 2-hydroxyethyl glycine, diazabicycloundecene, creatine, arginine ethyl ester, amantadine, rimantadine, ornithine, taurine, citrulline, or a combination or mixture thereof.

The pharmaceutical composition can comprise any stabilizing amount of a cation. In some embodiments, the pharmaceutical composition comprises a molar ratio of cation (e.g., $Ca^{2+}$ or a salt thereof) to linaclotide between 200:1 and 1:1. In some embodiments, the composition comprises a molar ratio of cation (e.g., $Ca^{2+}$ or a salt thereof) to linaclotide between 175:1 and 10:1. In some embodiments, the composition comprises a molar ratio of cation (e.g., $Ca^{2+}$ or a salt thereof) to linaclotide between 160:1 and 30:1. In some embodiments, the composition comprises a molar ratio of cation (e.g., $Ca^{2+}$ or a salt thereof) to linaclotide between 150:1 and 50:1. In some embodiments, the composition comprises a molar ratio of cation (e.g., $Ca^{2+}$ or a salt thereof) to linaclotide between 125:1 and 75:1. In some embodiments, the composition comprises a molar ratio of cation (e.g., $Ca^{2+}$ or a salt thereof) to linaclotide between 120:1 and 80:1. In some embodiments, the composition comprises a molar ratio of cation (e.g., $Ca^{2+}$ or a salt thereof) to linaclotide between 110:1 and 90:1.

In some embodiments, the composition (e.g., bead or granule) comprises 0.0001 to 2% by weight of $Ca^{2+}$ or a pharmaceutically acceptable salt thereof. In some embodiments, the composition comprises 0.0005 to 1.5 wt. % of $Ca^{2+}$ or a salt thereof. In some embodiments, the composition comprises 0.001 to 1 wt. % (e.g., 0.01 to 0.75 wt. %, 0.05 to 0.5 wt. %, 0.05 to 0.3 wt. %, 0.05 to 0.2 wt. %, 0.07 to 0.15 wt. %, or even about 0.1% by weight) of $Ca^{2+}$ or a salt thereof. In some embodiments, the pharmaceutical composition comprises a molar ratio of cation to linaclotide between 100:1 and 1:100. In some embodiments, the composition comprises a molar ratio of cation to linaclotide between 100:1 and 1:1. In some embodiments, the composition comprises a molar ratio of cation to linaclotide between 90:1 and 2:1. In some embodiments, the composition comprises a molar ratio of cation to linaclotide between 80:1 and 5:1. In some embodiments, the composition comprises a molar ratio of cation to linaclotide between 70:1 and 10:1. In some embodiments, the composition comprises a molar ratio of cation to linaclotide between 60:1 and 20:1. In some embodiments, the composition comprises a molar ratio of cation to linaclotide between 50:1 and 30:1. In some embodiments, the composition comprises a molar ratio of cation to linaclotide between 40:1 and 20:1. In some embodiments, the composition comprises a molar ratio of cation to linaclotide between 100:1 and 20:1. In some embodiments, the composition comprises a molar ratio of cation to linaclotide between 100:1 and 25:1. In some embodiments, the composition comprises a molar ratio of cation to linaclotide between 100:1 and 30:1. In some embodiments, the composition comprises a molar ratio of cation to linaclotide between 100:1 and 40:1. In some embodiments, the composition comprises a molar ratio of cation to linaclotide between 100:1 and 50:1. In some embodiments, the composition comprises a molar ratio of cation to linaclotide between 100:1 and 60:1. In some embodiments, the composition comprises a molar ratio of cation to linaclotide between 100:1 and 70:1. In some embodiments, the composition comprises a molar ratio of cation to linaclotide of at least 5:1. In some embodiments, the composition comprises a molar ratio of cation to linaclotide of at least 10:1. In some embodiments, the composition comprises a molar ratio of cation to linaclotide of at least 20:1. In some embodiments, the composition comprises a molar ratio of cation to linaclotide of at least 25:1. In some embodiments, the composition comprises a molar ratio of cation to linaclotide of at least 30:1. In some embodiments, the composition comprises a molar ratio of cation to linaclotide of at least 40:1. In some embodiments, the composition comprises a molar ratio of cation to linaclotide of at least 60:1.

The pharmaceutical composition can comprise any suitable polymer. Suitable polymers include, for example, polyvinyl pyrrolidone (PVP), polyvinyl alcohol (PVA), hydroxylpropyl methyl cellulose (HPMC), hydroxylpropyl cellulose (HPC), methyl cellulose, methacrylate polymers, cyclodextrin, dextrin, dextran, polyacrylic acid, chitosan, guar gum, xanthan gum, polyethylene oxide (e.g., polyethylene polypropylene oxide), poly (sodium vinylsulfonate), polyethylene glycol, poly(arginine), poly carbophil, polyvinyl pyrrolidone-co-vinyl acetate, a poloxamer (e.g., Pluronic® products available from BASF), alginate, trehalose, sucrose, inulin, or a combination or mixture thereof. In some embodiments, the composition comprises a polymer selected from PVP, PVA, methacrylate polymers, cyclodextrin, dextran, polyacrylic acid, chitosan, guar gum, xanthan gum, polyethylene oxide, polyethylene glycol, poly(arginine), poly carbophil, polyvinyl pyrrolidone-co-vinyl acetate, a poloxamer, or a combination or mixture thereof. In some embodiments, the composition comprises PVP, PVA, polyethylene oxide, or a mixture thereof. In some embodiments, the composition comprises PVP, PVA, or a mixture thereof. In some embodiments, the composition comprises PVP. In some embodiments, the composition comprises PVA.

The composition can contain any suitable amount of a polymer. In some embodiments, the composition (e.g., bead or granule) comprises 0.1 to 10% by weight of a polymer (for example, PVA or PVP). In some embodiments, the composition comprises 1 to 5 wt. % of a polymer component. In some embodiments, the composition comprises 2 to 5 wt. % (e.g., 3 to 5 wt. %, 3.5 to 4.5 wt. %, or about 4% by weight) of a polymer (e.g., PVA or PVP).

In some embodiments, the pharmaceutical composition comprises PVP and a stabilizing amount of an amino acid selected from meglumine, histidine or a mixture thereof. In some embodiments, the composition comprises PVP and a stabilizing amount of histidine. In some embodiments, the composition comprises PVP and a stabilizing amount of meglumine.

In some embodiments, the pharmaceutical composition comprises PVA and an amino acid selected from meglumine, histidine or a mixture thereof. In some embodiments, the composition comprises PVA and histidine. In some embodiments, the composition comprises PVA and meglumine.

In some embodiments, the pharmaceutical composition comprises a stabilizing amount of an amino acid selected from histidine, meglumine and combinations thereof; and a stabilizing amount of a cation (e.g., a metal cation, for example, a divalent metal cation selected from $Mg^{2+}$, $Ca^{2+}$, $Zn^{2+}$ or a salt thereof or a combination or mixture thereof). In some embodiments, the composition comprises a stabilizing amount of an amino acid selected from histidine, meglumine and combinations thereof; and a stabilizing amount of a divalent metal cation selected from $Mg^{2+}$, $Ca^{2+}$ or a salt thereof or a combination or mixture thereof. In some embodiments, the composition comprises a stabilizing amount of histidine, meglumine or a mixture thereof; and a divalent metal cation selected from $Ca^{2+}$, $Zn^{2+}$ or a salt thereof or a combination or mixture thereof. In some embodiments, the composition comprises a stabilizing amount of meglumine and a stabilizing amount of $Ca^{2+}$ or a salt thereof. In some embodiments, the composition comprises a stabilizing amount of histidine and a stabilizing amount of $Ca^{2+}$ or a salt thereof. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) between 2:1 and 1:2. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) between 1.75:1 and 1:1.75. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) between 1.5:1 and 1:1.5. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) between 1.25:1 and 1:1.25. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) between 1.1:1 and 1:1.1.

In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 5:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 4:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 3:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 2:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 1.75:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 1.5:1. In some embodiments, the composition comprises a cation and amino acid (e.g., meglumine, histidine or mixture thereof) in a molar ratio of cation:amino acid (e.g., $Ca^{2+}$:meglumine or $Ca^{2+}$:histidine) of less than 1.25:1.

In some preferred embodiments, the composition comprises a cation (e.g., $Ca^{2+}$) and an amino acid selected from meglumine, histidine or mixture thereof in a molar ratio of cation:amino acid (e.g., $Ca^{2+}$:meglumine or $Ca^{2+}$:histidine) between about 1.5:1 and 0.5:1. In some preferred embodiments, the composition comprises a cation (e.g., $Ca^{2+}$) and an amino acid selected from meglumine, histidine or mixture thereof in a molar ratio of cation:amino acid (e.g., $Ca^{2+}$:meglumine or $Ca^{2+}$:histidine) between about 1.4:1 and 0.6:1. In some preferred embodiments, the composition comprises a cation (e.g., $Ca^{2+}$) and an amino acid selected from meglumine, histidine or mixture thereof in a molar ratio of cation:amino acid (e.g., $Ca^{2+}$:meglumine or $Ca^{2+}$:histidine) between about 1.3:1 and 0.7:1. In some preferred embodiments, the composition comprises a cation (e.g., $Ca^{2+}$) and an amino acid selected from meglumine, histidine or mixture thereof in a molar ratio of cation:amino acid (e.g., $Ca^{2+}$:meglumine or $Ca^{2+}$:histidine) between about 1.2:1 and 0.8:1. In some preferred embodiments, the composition comprises a cation (e.g., $Ca^{2+}$) and an amino acid selected from meglumine, histidine or mixture thereof in a molar ratio of cation:amino acid (e.g., $Ca^{2+}$:meglumine or $Ca^{2+}$:histidine) between about 1.1:1 and 0.9:1.

In some embodiments, the pharmaceutical composition comprises (i) a polymer (e.g., PVP or PVA), (ii) a stabilizing amount of meglumine, histidine or a combination thereof, and (iii) a stabilizing amount of a cation (e.g., a divalent metal cation for example $Mg^{2+}$, $Ca^{2+}$, $Zn^{2+}$ or a pharmaceutically-acceptable salt thereof or a combination or mixture thereof). In some embodiments, the pharmaceutical composition comprises (i) a polymer (e.g., PVP and/or PVA), (ii) histidine or meglumine, and (iii) $Mg^{2+}$, $Ca^{2+}$, $Zn^{2+}$ or a salt thereof or a combination or mixture thereof. In some embodiments, the composition comprises a stabilizing amount of PVA and stabilizing amounts of meglumine, and a metal cation.

In some embodiments, the pharmaceutical composition (e.g., bead or granule) comprises linaclotide (e.g., a therapeutically effective amount of linaclotide, for example, between 0.01 μg and 300 μg, between 0.01 μg and 150 μg, or between 0.01 μg and 125 μg of linaclotide), histidine in a molar ratio to linaclotide between 150:1 and 50:1 (e.g., between 125:1 and 75:1, between 120:1 and 80:1, between 110:1 and 90:1 or a molar ratio of histidine to linaclotide of about 100:1), $Ca^{2+}$ or a salt thereof in a molar ratio to linaclotide between 150:1 and 50:1 (e.g., between 125:1 and 75:1, between 120:1 and 80:1, between 110:1 and 90:1 or a molar ratio of $Ca^{2+}$ or a salt thereof to linaclotide of about 100:1) and optionally a polymer (e.g., PVA or PVP).

In some embodiments, the pharmaceutical composition (e.g., bead or granule) comprises linaclotide (e.g., a therapeutically effective amount of linaclotide, for example, between 0.01 μg and 300 μg, between 0.01 μg and 150 μg, or between 0.01 μg and 125 μg of linaclotide), meglumine in a molar ratio to linaclotide between 150:1 and 50:1 (e.g., between 125:1 and 75:1, between 120:1 and 80:1, between 110:1 and 90:1 or even a molar ratio of meglumine to linaclotide of about 100:1), $Ca^{2+}$ or a salt thereof in a molar ratio to linaclotide between 150:1 and 50:1 (e.g., between 125:1 and 75:1, between 120:1 and 80:1, between 110:1 and 90:1 or a molar ratio of $Ca^{2+}$ or a salt thereof to linaclotide of about 100:1) and optionally a polymer (e.g., PVA or PVP).

In some embodiments, the composition (e.g., bead or granule) comprises linaclotide (e.g., a therapeutically effective amount of linaclotide, for example, between 0.01 μg and 300 μg, between 0.01 μg and 150 μg, or between 0.01 μg and 125 µg of linaclotide), an amino acid (e.g., meglumine or histidine) in a concentration of 0.005 to 0.05% by weight (e.g., 0.005 to 0.04 wt. %, 0.008 to 0.03 wt. %, 0.008 to 0.02 wt. %, 0.008 to 0.015 wt. %, 0.008 to 0.012 wt. %, or even about 0.01 wt. %), a metal cation (e.g., $Ca^{2+}$ or a salt thereof) in a concentration of 0.01 to 0.75% by weight (e.g., 0.05 to 0.5 wt. %, 0.05 to 0.3 wt. %, 0.05 to 0.2 wt. %, 0.07 to 0.15 wt. %, or even about 0.1% by weight) and optionally a polymer (e.g., PVA or PVP).

In some embodiments, the composition (e.g., bead or granule) comprises linaclotide (e.g., a therapeutically effective amount of linaclotide, for example, between 0.01 µg and 300 µg, between 0.01 µg and 150 µg, or between 0.01 µg and 125 µg of linaclotide), meglumine in a concentration of 0.005 to 0.05% by weight (e.g., 0.005 to 0.04 wt. %, 0.008 to 0.03 wt. %, 0.008 to 0.02 wt. %, 0.008 to 0.015 wt. %, 0.008 to 0.012 wt. %, or even about 0.01 wt. %), $Ca^{2+}$ or a salt thereof in a concentration of 0.01 to 0.75% by weight (e.g., 0.05 to 0.5 wt. %, 0.05 to 0.3 wt. %, 0.05 to 0.2 wt. %, 0.07 to 0.15 wt. %, or even about 0.1% by weight) and optionally a polymer (e.g., PVA or PVP).

In some embodiments, the composition (e.g., bead or granule) comprises linaclotide (e.g., a therapeutically effective amount of linaclotide, for example, between 0.01 µg and 300 µg, between 0.01 µg and 150 µg, or between 0.01 µg and 125 µg of linaclotide), histidine in a concentration of 0.005 to 0.05% by weight (e.g., 0.005 to 0.04 wt. %, 0.008 to 0.03 wt. %, 0.008 to 0.02 wt. %, 0.008 to 0.015 wt. %, 0.008 to 0.012 wt. %, or even about 0.01 wt. %), $Ca^{2+}$ or a salt thereof in a concentration of 0.01 to 0.75% by weight (e.g., 0.05 to 0.5 wt. %, 0.05 to 0.3 wt. %, 0.05 to 0.2 wt. %, 0.07 to 0.15 wt. %, or even about 0.1% by weight) and optionally a polymer (e.g., PVA or PVP).

The pharmaceutical composition may also comprise any one or more filling agents. Suitable filling agents include, but are not limited to, starch, calcium carbonate, calcium sulfate, hydroxylpropylmethyl cellulose, fructose, methyl cellulose, dextrates, dextrose, dextran, lactitol, maltose, sucrose, sorbitol, isomalt, pregelatinized starch, dicalcium phosphate, microcrystalline cellulose, mannitol, gelatin, trehalose, erythritol, maltitol, lactose, glucose, or a combination thereof, or a mixture thereof. In some embodiments, the filling agent is isomalt. In some embodiments, the filling agent is gelatin. In some embodiments, the filling agent is mannitol. In some embodiments, the filling agent is pregelatinized starch. In some embodiments, the filling agent is microcrystalline cellulose.

The pharmaceutical composition can comprise any suitable concentration of filling agent. In some embodiments, for example, the composition comprises one or more filling agents in a concentration of 0.1-99% by weight, relative to the total weight of the composition. In some embodiments, for example, the composition comprises one or more filling agents in a concentration of 1-95 wt. % of filling agent(s), relative to the total weight of the composition. In some embodiments, for example, the composition comprises one or more filling agents in a concentration of 10-90 wt. % of filling agent(s), relative to the total weight of the composition. In some embodiments, for example, the composition comprises one or more filling agents in a concentration of 20-90 wt. % of filling agent(s), relative to the total weight of the composition. In some embodiments, for example, the composition comprises one or more filling agents in a concentration of 25-85 wt. % of filling agent(s), relative to the total weight of the composition. In some embodiments, for example, the composition comprises one or more filling agents in a concentration of 30-80 wt. % of filling agent(s), relative to the total weight of the composition. In some embodiments, for example, the composition comprises one or more filling agents in a concentration of 40-70 wt. % of filling agent(s), relative to the total weight of the composition. In some embodiments, for example, the composition comprises one or more filling agents in a concentration of 10-60 wt. % of filling agent(s), relative to the total weight of the composition. In some embodiments, for example, the composition comprises one or more filling agents in a concentration of 20-50 wt. % of filling agent(s), relative to the total weight of the composition. In some embodiments, the composition comprises one or more filling agents in a concentration of at least 20 wt. %, for example, at least 40 wt. %, at least 60 wt. %, at least 70 wt. %, at least 80 wt. %, or at least 90 wt. %, relative to the total weight of the composition.

In some embodiments, the pharmaceutical composition (e.g., orally disintegrating composition) can comprise one or more plasticizers. Suitable plasticizers include, but are not limited to, polyethylene glycol, propylene glycol, glycerin, glycerol, monoacetin, diacetin, triacetin, dimethyl phthalate, diethyl phthalate, dibutyl phthalate, dibutyl sebacate, triethyl titrate, tributyl citrate, triethyl citrate, triethyl acetyl citrate, castor oil, acetylated monoglycerides, sorbitol or combinations thereof. In exemplary embodiments, the concentration of the plasticizer in the formulation may be about 0 to about 30 wt %, for example, about 1 to about 20 wt %, about 0.1 to about 10 wt %, about 1 to about 5 wt %, or even 0.1 to about 4 wt %.

In some embodiments, the pharmaceutical composition is an orally-disintegrating composition and comprises a film-forming agent, a water-soluble polymer, a combination of two or more water-soluble polymers or a combination of a water-soluble polymer and a water-insoluble or poorly-soluble polymer. Water-soluble polymers that may be used in the orally-dissolving formulations of the present invention include, but are not limited to, cellulose derivatives, synthetic polymers polyacrylates and natural gums. For example, the water-soluble polymers used in the orally-dissolving formulations of the present invention may include, but are not limited to, methyl cellulose, hydroxypropyl cellulose, hydroxypropylmethyl cellulose, ethyl cellulose, hydroxyethyl cellulose, hydroxypropyl cellulose, carboxymethyl cellulose, cellulose acetate phthalate, cellulose acetate butyrate, amylose, dextran, casein, pullulan, gelatin, pectin, agar, carrageenan, xanthan gum, tragacanth, guar gum, acacia gum, arabic gum, polyethylene glycol, polyethylene oxide, polyvinyl pyrrolidone, polyvinyl alcohol, cyclodextrin, carboxyvinyl polymers, sodium alginate, polyacrylic acid, methylmethacrylate or mixtures thereof. In exemplary embodiments, the concentration of the water-soluble polymer in the formulation may be about 20% to about 90% (by weight), preferably between about 40% to about 80% (by weight).

One skilled in the art, with the benefit of this disclosure, will understand that other components may be included to enhance one or more properties of the pharmaceutical compositions. In some embodiments, for example, the pharmaceutical composition may include one or more disintegrants, lubricants, anti-caking additives, anti-microbial agents, anti-foaming agents, emulsifiers, surfactants, buffering agents, and/or coloring agents.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof. In some embodiments, the disintegrant is crospovidone. In some embodiments, the disintegrant is croscarmellose sodium.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable anti-caking additives include, for example, calcium silicate, magnesium silicate, silicon dioxide, colloidal silicon dioxide, talc, and mixtures thereof. In some embodiments, the composition comprises about 0.01 wt. % to about 5 wt. % of an anti-caking additive (e.g., talc). In some embodiments, the composition comprises about 0.05 wt. % to about 2 wt. % of an anti-caking additive (e.g., talc). In some embodiments, the composition comprises about 0.1 wt. % to about 1 wt. % of an anti-caking additive (e.g., talc). In some embodiments, the composition comprises about 0.25 wt. % to about 0.75 wt. % (e.g., about 0.5 wt. %) of an anti-caking additive (e.g., talc).

Suitable anti-microbial additives that may be used, e.g., as a preservative for the linaclotide compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

In some embodiments, the pharmaceutical composition (e.g., orally-disintegrating composition) may comprise a taste-masking agent. Generally, any natural or synthetic flavoring agent or sweetening agent known in the art may be used in the pharmaceutical compositions of the present invention. For example, suitable taste-masking agents include, but are not limited to, essential oils, water-soluble extracts, sugar, monosaccharides, oligosaccharides, aldose, ketose, dextrose, maltose, lactose, glucose, fructose, sucrose, mannitol xylitol, D-sorbitol, erythritol, pentitol, hexitol, malitol, acesulfame potassium, talin, glycyrrhizin, sucralose, aspartame, saccharin, sodium saccharin, sodium cyclamate, eugenyl formate aldehyde flavorings and combinations thereof.

Exemplary aldehyde flavorings that may be used include, but are not limited to acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin). In some embodiments, the taste-masking agents may include combination of acesulfame potassium and flavors. One skilled in the art with the benefit of the present disclosure will appreciate that other and further ingredients may be included in the pharmaceutical composition of the present invention, for example, a matrix-forming polymer permeation enhancer, substance for imparting mucoadhesive properties, or other auxiliary substances.

The composition may also comprise any suitable pharmaceutically acceptable carrier or medium. Suitable pharmaceutically acceptable carriers include, for example, any solvents, dispersants, pH-buffering agents, coatings, absorption-promoting agents, controlled-release agents, and one or more inert excipients (e.g., filling agents, starches, polyols, granulating agents, microcrystalline cellulose, diluents, lubricants, binders, disintegrating agents), or the like. In addition, the compositions can contain any desired additional components, additives, and/or species, for example, surface active additives, dispersing additives, humectants, suspending agents, solubilizers, buffering agents, disintegrants, preservatives, colorants, flavorants, and the like. In some embodiments, the composition comprises one or more ion species that interact with linaclotide.

The composition can also comprise any suitable pH buffering agent. In some embodiments, the pH buffering agent is present in the composition in an amount sufficient to achieve the isoelectric point of linaclotide. In the regard, the composition can have any desired pH. In some embodiments, the composition has a pH of 2 to 5 (for example, a pH of 2 to 4.5, a pH of 2 4o 4, a pH of 2.5 to 4, a pH of 2.5 to 3.5, a pH of 2.5 to 3, or even a pH of 3).

In some embodiments, the composition comprises linaclotide and a hydrolysis product, e.g., a hydrolysis product comprising or having a structure of:

(SEQ ID NO: 2)

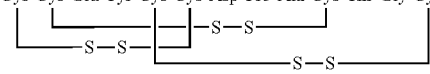

H—Cys-Cys-Glu-Tyr-Cys-Cys-Asp-Pro-Ala-Cys-Thr-Gly-Cys-Tyr—OH.

The composition can contain any desired concentration of the hydrolysis product. In some embodiments, the composition comprises less than 10 wt. % of the hydrolysis product. In some embodiments, the composition comprises less than 7 wt. % of the hydrolysis product. In some embodiments, the composition comprises less than 6 wt. % of the hydrolysis product. In some embodiments, the composition comprises less than 5 wt. % of the hydrolysis product. In some embodiments, the composition comprises less than 4 wt. % of the hydrolysis product. In some embodiments, the composition comprises less than 3 wt. % of the hydrolysis product. In some embodiments, the composition comprises less than 2 wt. % of the hydrolysis product. In some embodiments, the composition comprises less than 1 wt. % of the hydrolysis product. In some embodiments, the composition comprises between 0.01 and 10 wt. % of the hydrolysis product. In some embodiments, the composition comprises between 0.1 and 7 wt. % of the hydrolysis product. In some embodiments, the composition comprises between 0.1 and 5 wt. % of the hydrolysis product. In some embodiments, the composition comprises between 0.5 and 5 wt. % of the hydrolysis product. In some embodiments, the composition comprises between 1 and 5 wt. % of the hydrolysis product. In some embodiments, the composition comprises between 0.1 and 4 wt. % of the hydrolysis product. In some embodiments, the composition comprises between 0.5 and 4 wt. % of the hydrolysis product. In some embodiments, the composition comprises between 1 and 4 wt. % of the hydrolysis product. In some embodiments, the composition comprises between 0.1 and 3 wt. % of the hydrolysis product. In some embodiments, the composition comprises between 0.5 and 3 wt. % of the hydrolysis product. In some embodiments, the composition comprises between 1 and 3 wt. % of the hydrolysis product. In some embodiments, the composition comprises between 0.1 and 2.5 wt. % of the hydrolysis product. In some embodiments, the composition comprises between 0.5 and 2.5 wt. % of the hydrolysis product. In some embodiments, the composition comprises between 1 and 2.5 wt. % of the hydrolysis product. In some embodiments, the composition comprises between 0.1 and 2 wt. % of the hydrolysis product. In some embodiments, the composition comprises between 0.5 and 2 wt. % of the hydrolysis product. In some embodiments, the composition comprises between 1 and 2 wt. % of the hydrolysis product. In some embodiments, the composition comprises between 0.1 and 1.5 wt. % of the hydrolysis product. In some embodiments, the composition comprises between 0.5 and 1.5 wt. % of the hydrolysis product. In some embodiments, the composition comprises between 0.1 and 1 wt. % of the hydrolysis product. In some embodiments, the composition comprises between 0.5 and 1 wt. % of the hydrolysis product.

In some embodiments, the composition comprises linaclotide and a formaldehyde imine product, e.g., a formaldehyde imine product comprising or having a structure of:

(SEQ ID NO: 3)

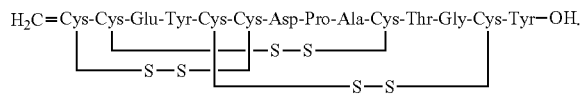

The composition can contain any desired concentration of the formaldehyde imine product. In some embodiments, the composition comprises less than 10 wt. % of the formaldehyde imine product. In some embodiments, the composition comprises less than 7 wt. % of the formaldehyde imine product. In some embodiments, the composition comprises less than 6 wt. % of the formaldehyde imine product. In some embodiments, the composition comprises less than 5 wt. % of the formaldehyde imine product. In some embodiments, the composition comprises less than 4 wt. % of the formaldehyde imine product. In some embodiments, the composition comprises less than 3 wt. % of the formaldehyde imine product. In some embodiments, the composition comprises less than 2 wt. % of the formaldehyde imine product. In some embodiments, the composition comprises less than 1 wt. % of the formaldehyde imine product. In some embodiments, the composition comprises between 0.01 and 10 wt. % of the formaldehyde imine product. In some embodiments, the composition comprises between 0.1 and 7 wt. % of the formaldehyde imine product. In some embodiments, the composition comprises between 0.1 and 5 wt. % of the formaldehyde imine product. In some embodiments, the composition comprises between 0.5 and 5 wt. % of the formaldehyde imine product. In some embodiments, the composition comprises between 1 and 5 wt. % of the formaldehyde imine product. In some embodiments, the composition comprises between 0.1 and 4 wt. % of the formaldehyde imine product. In some embodiments, the composition comprises between 0.5 and 4 wt. % of the formaldehyde imine product. In some embodiments, the composition comprises between 1 and 4 wt. % of the formaldehyde imine product. In some embodiments, the composition comprises between 0.1 and 3 wt. % of the formaldehyde imine product. In some embodiments, the composition comprises between 0.5 and 3 wt. % of the formaldehyde imine product. In some embodiments, the composition comprises between 1 and 3 wt. % of the formaldehyde imine product. In some embodiments, the composition comprises between 0.1 and 2.5 wt. % of the formaldehyde imine product. In some embodiments, the composition comprises between 0.5 and 2.5 wt. % of the formaldehyde imine product. In some embodiments, the composition comprises between 1 and 2.5 wt. % of the formaldehyde imine product. In some embodiments, the composition comprises between 0.1 and 2 wt. % of the formaldehyde imine product. In some embodiments, the composition comprises between 0.5 and 2 wt. % of the formaldehyde imine product. In some embodiments, the composition comprises between 1 and 2 wt. % of the formaldehyde imine product. In some embodiments, the composition comprises between 0.1 and 1.5 wt. % of the formaldehyde imine product. In some embodiments, the composition comprises between 0.5 and 1.5 wt. % of the formaldehyde imine product. In some embodiments, the composition comprises between 0.1 and 1 wt. % of the formaldehyde imine product. In some embodiments, the composition comprises between 0.5 and 1 wt. % of the formaldehyde imine product.

In some embodiments, the composition comprises linaclotide and a peptide modified with the addition of methylene at the α-amine group of the N-terminal $Cys_1$ that is cross-linked to the amine group of $Cys_2$ to form an imidazolidinone 5 membered ring at the N-terminus of the peptide ("$Cys_1$-IMD product") comprising or having a structure of:

(SEQ ID NO: 5)

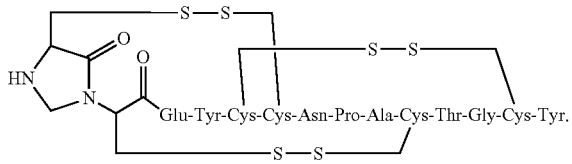

The composition can contain any desired concentration of the $Cys_1$-IMD product. In some embodiments, the composition comprises less than 10 wt. % of the $Cys_1$-IMD product. In some embodiments, the composition comprises less than 7 wt. % of the $Cys_1$-IMD product. In some embodiments, the composition comprises less than 6 wt. % of the $Cys_1$-IMD product. In some embodiments, the composition comprises less than 5 wt. % of the $Cys_1$-IMD product. In some embodiments, the composition comprises less than 4 wt. % of the $Cys_1$-IMD product. In some embodiments, the composition comprises less than 3 wt. % of the $Cys_1$-IMD product. In some embodiments, the composition comprises less than 2 wt. % of the $Cys_1$-IMD product. In some embodiments, the composition comprises less than 1 wt. % of the $Cys_1$-IMD product. In some embodiments, the composition comprises between 0.01 and 10 wt. % of the $Cys_1$-IMD product. In some embodiments, the composition comprises between 0.1 and 7 wt. % of the $Cys_1$-IMD product.

In some embodiments, the composition comprises between 0.1 and 5 wt. % of the $Cys_1$-IMD product. In some embodiments, the composition comprises between 0.5 and 5 wt. % of the $Cys_1$-IMD product. In some embodiments, the composition comprises between 1 and 5 wt. % of the $Cys_1$-IMD product. In some embodiments, the composition comprises between 0.1 and 4 wt. % of the $Cys_1$-IMD product. In some embodiments, the composition comprises between 0.5 and 4 wt. % of the $Cys_1$-IMD product. In some embodiments, the composition comprises between 1 and 4 wt. % of the $Cys_1$-IMD product. In some embodiments, the composition comprises between 0.1 and 3 wt. % of the $Cys_1$-IMD product. In some embodiments, the composition comprises between 0.5 and 3 wt. % of the $Cys_1$-IMD product. In some embodiments, the composition comprises between 1 and 3 wt. % of the $Cys_1$-IMD product. In some embodiments, the composition comprises between 0.1 and 2.5 wt. % of the $Cys_1$-IMD product. In some embodiments, the composition comprises between 0.5 and 2.5 wt. % of the $Cys_1$-IMD product. In some embodiments, the composition comprises between 1 and 2.5 wt. % of the $Cys_1$-IMD product. In some embodiments, the composition comprises between 0.1 and 2 wt. % of the $Cys_1$-IMD product. In some embodiments, the composition comprises between 0.5 and 2 wt. % of the $Cys_1$-IMD product. In some embodiments, the composition comprises between 1 and 2 wt. % of the $Cys_1$-IMD product. In some embodiments, the composition comprises between 0.1 and 1.5 wt. % of the $Cys_1$-IMD product. In some embodiments, the composition comprises between 0.5 and 1.5 wt. % of the $Cys_1$-IMD product. In some embodiments, the composition comprises between 0.1 and 1 wt. % of the $Cys_1$-IMD product. In some embodiments, the composition comprises between 0.5 and 1 wt. % of the $Cys_1$-IMD product.

In some embodiments, the composition comprises linaclotide and an oxidation product, e.g., an oxidation product comprising or having a structure of:

(SEQ ID NO: 4)

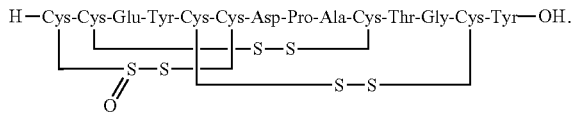

In some embodiments, the composition comprises less than 3 wt. % of the oxidation product. In some embodiments, the composition comprises less than 2 wt. % of the oxidation product. In some embodiments, the composition comprises less than 1 wt. % of the oxidation product. In some embodiments, the composition comprises between 0.01 and 10 wt. % of the oxidation product. In some embodiments, the composition comprises between 0.1 and 7 wt. % of the oxidation product. In some embodiments, the composition comprises between 0.1 and 5 wt. % of the oxidation product. In some embodiments, the composition comprises between 0.5 and 5 wt. % of the oxidation product. In some embodiments, the composition comprises between 1 and 5 wt. % of the oxidation product. In some embodiments, the composition comprises between 0.1 and 4 wt. % of the oxidation product. In some embodiments, the composition comprises between 0.5 and 4 wt. % of the oxidation product. In some embodiments, the composition comprises between 1 and 4 wt. % of the oxidation product. In some embodiments, the composition comprises between 0.1 and 3 wt. % of the oxidation product. In some embodiments, the composition comprises between 0.5 and 3 wt. % of the oxidation product. In some embodiments, the composition comprises between 1 and 3 wt. % of the oxidation product. In some embodiments, the composition comprises between 0.1 and 2.5 wt. % of the oxidation product. In some embodiments, the composition comprises between 0.5 and 2.5 wt. % of the oxidation product. In some embodiments, the composition comprises between 1 and 2.5 wt. % of the oxidation product. In some embodiments, the composition comprises between 0.1 and 2 wt. % of the oxidation product. In some embodiments, the composition comprises between 0.5 and 2 wt. % of the oxidation product. In some embodiments, the composition comprises between 1 and 2 wt. % of the oxidation product. In some embodiments, the composition comprises between 0.1 and 1.5 wt. % of the oxidation product. In some embodiments, the composition comprises between 0.5 and 1.5 wt. % of the oxidation product. In some embodiments, the composition comprises between 0.1 and 1 wt. % of the oxidation product. In some embodiments, the composition comprises between 0.5 and 1 wt. % of the oxidation product.

In some embodiments, the composition comprises linaclotide and an acetylation product, e.g., an acetylation product comprising or having a structure of:

(SEQ ID NO: 6)

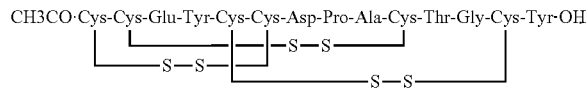

Alternatively, or in addition, the composition comprises linaclotide and an oxidation product having the depicted structure but wherein oxidation occurs at any one or more of the six depicted cysteinyl sulfurs. The composition can contain any desired concentration of the oxidation product. In some embodiments, the composition comprises less than 10 wt. % of the oxidation product. In some embodiments, the composition comprises less than 7 wt. % of the oxidation product. In some embodiments, the composition comprises less than 6 wt. % of the oxidation product. In some embodiments, the composition comprises less than 5 wt. % of the oxidation product. In some embodiments, the composition comprises less than 4 wt. % of the oxidation product. In The composition can contain any desired concentration of the acetylation product. In some embodiments, the composition comprises less than 10 wt. % of the acetylation product. In some embodiments, the composition comprises less than 7 wt. % of the acetylation product. In some embodiments, the composition comprises less than 6 wt. % of the acetylation product. In some embodiments, the composition comprises less than 5 wt. % of the acetylation product. In some embodiments, the composition comprises less than 4 wt. % of the acetylation product. In some embodiments, the composition comprises less than 3 wt. % of the acetylation product. In some embodiments, the composition comprises less than 2 wt. % of the acetylation product. In some embodiments, the composition comprises less than 1 wt. % of the acetylation product. In some embodiments, the composition comprises between 0.01 and 10 wt. % of the acetylation product. In some embodiments, the composition comprises between 0.1 and 7 wt. % of the acetylation product. In some embodiments, the composition comprises between 0.1 and 5 wt. % of the acetylation product. In some embodiments, the composition comprises between 0.5 and 5 wt. % of the acetylation product. In some embodiments, the composition comprises between 1 and 5 wt. % of the acetylation product. In some embodiments, the composition comprises between 0.1 and 4 wt. % of the acetylation product. In some embodiments, the composition comprises between 0.5 and 4 wt. % of the acetylation product. In some embodiments, the composition comprises between 1 and 4 wt. % of the acetylation product: In some embodiments, the composition comprises between 0.1 and 3 wt. % of the acetylation product. In some embodiments, the composition comprises between 0.5 and 3 wt. % of the acetylation product. In some embodiments, the composition comprises between 1 and 3 wt. % of the acetylation product. In some embodiments, the composition comprises between 0.1 and 2.5 wt. % of the acetylation product. In some embodiments, the composition comprises between 0.5 and 2.5 wt. % of the acetylation product. In some embodiments, the composition comprises between 1 and 2.5 wt. % of the acetylation product. In some embodiments, the composition comprises between 0.1 and 2 wt. % of the acetylation product. In some embodiments, the composition comprises between 0.5 and 2 wt. % of the acetylation product. In some embodiments, the composition comprises between 1 and 2 wt. % of the acetylation product. In some embodiments, the composition comprises between 0.1 and 1.5 wt. % of the acetylation product. In some embodiments, the composition comprises between 0.5 and 1.5 wt. % of the acetylation product. In some embodiments, the composition comprises between 0.1 and 1 wt. % of the acetylation product. In some embodiments, the composition comprises between 0.5 and 1 wt. % of the acetylation product.

In some embodiments, the composition comprises linaclotide and any desired concentration of multimers. In some embodiments, the composition comprises less than 10 wt. % of multimer(s). In some embodiments, the composition comprises less than 7 wt. % of multimer(s). In some embodiments, the composition comprises less than 6 wt. % of multimer(s). In some embodiments, the composition comprises less than 5 wt. % of multimer(s). In some embodiments, the composition comprises less than 4 wt. % of multimer(s). In some embodiments, the composition comprises less than 3 wt. % of multimer(s). In some embodiments, the composition comprises less than 2 wt. % of multimer(s). In some embodiments, the composition comprises less than 1 wt. % of multimer(s). In some embodiments, the composition comprises between 0.01 and 10 wt. % of multimer(s). In some embodiments, the composition comprises between 0.1 and 7 wt. % of multimer(s). In some embodiments, the composition comprises between 0.1 and 5 wt. % of multimer(s). In some embodiments, the composition comprises between 0.5 and 5 wt. % of multimer(s). In some embodiments, the composition comprises between 1 and 5 wt. % of multimer(s). In some embodiments, the composition comprises between 0.1 and 4 wt. % of multimer(s). In some embodiments, the composition comprises between 0.5 and 4 wt. % of multimer(s). In some embodiments, the composition comprises between 1 and 4 wt. % of multimer(s). In some embodiments, the composition comprises between 0.1 and 3 wt. % of multimer(s). In some embodiments, the composition comprises between 0.5 and 3 wt. % of multimer(s). In some embodiments, the composition comprises between 1 and 3 wt. % of multimer(s). In some embodiments, the composition comprises between 0.1 and 2.5 wt. % of multimer(s). In some embodiments, the composition comprises between 0.5 and 2.5 wt. % of multimer(s). In some embodiments, the composition comprises between 1 and 2.5 wt. % of multimer(s). In some embodiments, the composition comprises between 0.1 and 2 wt. % of multimer(s). In some embodiments, the composition comprises between 0.5 and 2 wt. % of multimer(s). In some embodiments, the composition comprises between 1 and 2 wt. % of multimer(s). In some embodiments, the composition comprises between 0.1 and 1.5 wt. % of multimer(s). In some embodiments, the composition comprises between 0.5 and 1.5 wt. % of multimer(s). In some embodiments, the composition comprises between 0.1 and 1 wt. % of multimer(s). In some embodiments, the composition comprises between 0.5 and 1 wt. % of multimer(s).

In some embodiments, the composition comprises an effective amount of linaclotide and any desired amount of reduced form linaclotide. As used herein, the term "reduced form linaclotide" refers to linaclotide having no disulfide bonds between cysteine amino acids. In some embodiments, the composition comprises less than 10 wt. % of reduced form linaclotide. In some embodiments, the composition comprises less than 7 wt. % of reduced form linaclotide. In some embodiments, the composition comprises less than 6 wt. % of reduced form linaclotide. In some embodiments, the composition comprises less than 5 wt. % of reduced form linaclotide. In some embodiments, the composition comprises less than 4 wt. % of reduced form linaclotide. In some embodiments, the composition comprises less than 3 wt. % of reduced form linaclotide. In some embodiments, the composition comprises less than 2 wt. % of reduced form linaclotide. In some embodiments, the composition comprises less than 1 wt. % of reduced form linaclotide. In some embodiments, the composition comprises between 0.01 and 10 wt. % of reduced form linaclotide. In some embodiments, the composition comprises between 0.1 and 7 wt. % of reduced form linaclotide. In some embodiments, the composition comprises between 0.1 and 5 wt. % of reduced form linaclotide. In some embodiments, the composition comprises between 0.5 and 5 wt. % of reduced form linaclotide. In some embodiments, the composition comprises between 1 and 5 wt. % of reduced form linaclotide. In some embodiments, the composition comprises between 0.1 and 4 wt. % of reduced form linaclotide. In some embodiments, the composition comprises between 0.5 and 4 wt. % of reduced form linaclotide. In some embodiments, the composition comprises between 1 and 4 wt. % of reduced form linaclotide. In some embodiments, the composition comprises between 0.1 and 3 wt. % of reduced form linaclotide. In some embodiments, the composition comprises between 0.5 and 3 wt. % of reduced form linaclotide. In some embodiments, the composition comprises between 1 and 3 wt. % of reduced form linaclotide. In some embodiments, the composition comprises between 0.1 and 2.5 wt. % of reduced form linaclotide. In some embodiments, the composition comprises between 0.5 and 2.5 wt. % of reduced form linaclotide. In some embodiments, the composition comprises between 1 and 2.5 wt. % of reduced form linaclotide. In some embodiments, the composition comprises between 0.1 and 2 wt. % of reduced form linaclotide. In some embodiments, the composition comprises between 0.5 and 2 wt. % of reduced form linaclotide. In some embodiments, the composition comprises between 1 and 2 wt. % of reduced form linaclotide. In some embodiments, the composition comprises between 0.1 and 1.5 wt. % of reduced form linaclotide. In some embodiments, the composition comprises between 0.5 and 1.5 wt. % of reduced form linaclotide. In some embodiments, the composition comprises between 0.1 and 1 wt. % of reduced form linaclotide. In some embodiments, the composition comprises between 0.5 and 1 wt. % of reduced form linaclotide.

In some embodiments, the composition comprises an effective amount of linaclotide and any desired amount of scrambled-form linaclotide. As used herein, the term "scrambled-form linaclotide" refers to linaclotide having disulfide bonds between $Cys_1$ and $Cys_{10}$, between $Cys_1$ and $Cys_{13}$, between $Cys_1$ and $Cys_5$, between $Cys_1$ and $Cys_2$, between $Cys_2$ and $Cys_6$, between $Cys_2$ and $Cys_{13}$, between $Cys_2$ and $Cys_5$, between $Cys_5$ and $Cys_6$, and/or between $Cys_5$ and $Cys_{10}$. In some embodiments, the composition comprises less than 10 wt. % of scrambled-form linaclotide. In some embodiments, the composition comprises less than 7 wt. % of scrambled-form linaclotide. In some embodiments, the composition comprises less than 6 wt. % of scrambled-form linaclotide. In some embodiments, the composition comprises less than 5 wt. % of scrambled-form linaclotide. In some embodiments, the composition comprises less than 4 wt. % of scrambled-form linaclotide. In some embodiments, the composition comprises less than 3 wt. % of scrambled-form linaclotide. In some embodiments, the composition comprises less than 2 wt. % of scrambled-form linaclotide. In some embodiments, the composition comprises less than 1 wt. % of scrambled-form linaclotide. In some embodiments, the composition comprises between 0.01 and 10 wt. % of scrambled-form linaclotide. In some embodiments, the composition comprises between 0.1 and 7 wt. % of scrambled-form linaclotide. In some embodiments, the composition comprises between 0.1 and 5 wt. % of scrambled-form linaclotide. In some embodiments, the composition comprises between 0.5 and 5 wt. % of scrambled-form linaclotide. In some embodiments, the composition comprises between 1 and 5 wt. % of scrambled-form linaclotide. In some embodiments, the composition comprises between 0.1 and 4 wt. % of scrambled-form linaclotide. In some embodiments, the composition comprises between 0.5 and 4 wt. % of scrambled-form linaclotide. In some embodiments, the composition comprises between 1 and 4 wt. % of scrambled-form linaclotide. In some embodiments, the composition comprises between 0.1 and 3 wt. % of scrambled-form linaclotide. In some embodiments, the composition comprises between 0.5 and 3 wt. % of scrambled-form linaclotide. In some embodiments, the composition comprises between 1 and 3 wt. % of scrambled-form linaclotide. In some embodiments, the composition comprises between 0.1 and 2.5 wt. % of scrambled-form linaclotide. In some embodiments, the composition comprises between 0.5 and 2.5 wt. % of scrambled-form linaclotide. In some embodiments, the composition comprises between 1 and 2.5 wt. % of scrambled-form linaclotide. In some embodiments, the composition comprises between 0.1 and 2 wt. % of scrambled-form linaclotide. In some embodiments, the composition comprises between 0.5 and 2 wt. % of scrambled-form linaclotide. In some embodiments, the composition comprises between 1 and 2 wt. % of scrambled-form linaclotide. In some embodiments, the composition comprises between 0.1 and 1.5 wt. % of scrambled-form linaclotide. In some embodiments, the composition comprises between 0.5 and 1.5 wt. % of scrambled-form linaclotide. In some embodiments, the composition comprises between 0.1 and 1 wt. % of scrambled-form linaclotide. In some embodiments, the composition comprises between 0.5 and 1 wt. % of scrambled-form linaclotide.

In some embodiments, the composition comprises a total degradant concentration of less than about 10 wt. %. In some embodiments, the composition comprises a total degradant concentration of less than about 8 wt. %. In some embodiments, the composition comprises a total degradant concentration of less than about 7 wt. %. In some embodiments, the composition comprises a total degradant concentration of less than about 6.5 wt. %. In some embodiments, the composition comprises a total degradant concentration of less than about 6 wt. %. In some embodiments, the composition comprises a total degradant concentration of less than about 5.5 wt. %. In some embodiments, the composition comprises a total degradant concentration of less than about 5 wt. %. In some embodiments, the composition comprises a total degradant concentration of less than about 4 wt. %. In some embodiments, the composition comprises a total degradant concentration of less than about 3 wt. %. In some embodiments, the composition comprises a total degradant concentration of less than about 2.5 wt. %. In some embodiments, the composition comprises a total degradant concentration of less than about 2 wt. %. In some embodiments, the composition comprises a total degradant concentration of less than about 1 wt. %.

The pharmaceutical composition can be used to treat and diseases, disorders and conditions that are responsive to treatment with agonists of the GC-C receptor. For example, the composition can be used to treat gastrointestinal disorders including, but not limited to, irritable bowel syndrome, constipation-predominant irritable bowel syndrome, dyspepsia (including functional dyspepsia or non-ulcer dyspepsia), gastrointestinal motility disorders, functional gastrointestinal disorders, gastroesophageal reflux disease (GERD), Crohn's disease, ulcerative colitis, inflammatory bowel disease, functional heartburn, gastroparesis, chronic intestinal pseudo-obstruction (or colonic pseudo-obstruction), and disorders and conditions associated with constipation, for example, chronic constipation, opioid induced constipation, post-surgical constipation (post-operative ileus), constipation associated with neuropathic disorders or a combination of symptoms thereof (such as a combination of irritable bowel syndrome and chronic constipation), or inflammation or pain associated therewith. In some embodiments, a method is provided for treating gastrointestinal disorders in a patient (e.g., mammal or human) diagnosed with one or more gastrointestinal disorders or conditions, wherein the method comprises administering an effective amount of the composition to the patient.

In another embodiment, a method is provided for increasing intestinal motility in a patient in need thereof, comprising administering an effective amount of the composition to the patient. Intestinal motility involves spontaneous coordinated dissentions and contractions of the stomach, intestines, colon and rectum to move food through the gastrointestinal tract during the digestive process.

In some embodiments, the methods may comprise administering a therapeutically effective amount of the pharmaceutical composition to a patient in need thereof.

An effective amount of a composition comprising linaclotide or a pharmaceutically acceptable salt thereof required to achieve desired results (such as desired treatment and/or symptom relief) of a subject is dependent on several understood factors, such as the identity and severity of the disorder being treated, as well as the age, weight, etc., of the patient being treated.

A subject or patient in whom administration of the pharmaceutical composition is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions described herein are particularly suited for administration to any animal, particularly a mammal, and including, but by no means limited to, humans, rodents and non-rodents, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., e.g., for veterinary medical use.

In some embodiments, the effective dose range of linaclotide for adult humans is from 25 µg to 6 mg per day orally. In some embodiments, the dose range is 25 µg to 2 mg per day orally. In some embodiments, the dose range for adult humans is 50 µg to 1 mg per day orally (e.g., 50 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg or 1 mg). In some embodiments, the dose range is 100 µg to 600 µg per day orally. In some embodiments, the dose is 50 µg, 100 µg, 150 µg, 200 pig, 300 µg, 400 µg, 500 µg or 600 µg linaclotide per day orally. In some embodiments, the dose is 50 µg linaclotide per day orally. In some embodiments, the dose is 100 µg linaclotide per day orally. In some embodiments, the dose is 150 µg linaclotide per day orally. In some embodiments, the dose is 200 µg linaclotide per day orally. In some embodiments, the dose is 300 µg linaclotide per day orally. In some embodiments, the dose is 400 µg linaclotide per day orally. In some embodiments, the dose is 500 µg linaclotide per day orally. In some embodiments, the dose is 600 µg linaclotide per day orally.

In some embodiments, the effective pediatric dose range of linaclotide is from 0.05 µg to 2 mg per day orally. In some embodiments, the effective pediatric dose range of linaclotide is from 0.05 µg to 100 µg per day orally. In some embodiments, the effective pediatric dose range of linaclotide is from 0.1 µg to 90 µg per day orally. In some embodiments, the effective pediatric dose range of linaclotide is from 0.1 µg to 50 µg per day orally. In some embodiments, the effective pediatric dose range of linaclotide is from 0.1 µg to 25 µg per day orally. In some embodiments, the effective pediatric dose range of linaclotide is from 0.1 µg to 10 µg per day orally. In some embodiments, the effective pediatric dose range of linaclotide is from 0.1 µg to 5 µg per day orally. In some embodiments, the effective pediatric dose range of linaclotide is from 0.1 µg to 1 µg per day orally. In some embodiments, the effective pediatric dose range of linaclotide is from 0.1 µg to 0.5 µg per day orally. In some embodiments, the effective pediatric dose range of linaclotide is 0.1 µg per day orally. In some embodiments, the effective pediatric dose range of linaclotide is 0.15 µg per day orally. In some embodiments, the effective pediatric dose range of linaclotide is 0.25 µg per day orally. In some embodiments, the effective pediatric dose range of linaclotide is 0.5 µg per day orally. In some embodiments, the effective pediatric dose range of linaclotide is 3.5 µg per day orally. In some embodiments, the effective pediatric dose range of linaclotide is 15 µg per day orally. In some embodiments, the effective pediatric dose range of linaclotide is 45 µg per day orally. In some embodiments, the effective pediatric dose range of linaclotide is 60 µg per day orally. In some embodiments, the effective pediatric dose range of linaclotide is 90 µg per day orally.

In some embodiments, the unit dosage form and daily dose are equivalent. In some embodiments, the unit dosage form is administered with food at anytime of the day, without food at anytime of the day, with food after an overnight fast (e.g., with breakfast). In some embodiments, the unit dosage form is administered once a day, twice a day or three times a day. In some embodiments, one, two or three unit dosage forms will contain the daily oral dose of linaclotide. The precise amount of compound administered to a patient will be the responsibility of the attendant physician. However, the dose employed will depend on a number of factors, including the age and sex of the patient, the precise disorder being treated, and its severity.

In some embodiments, the compositions are administered as a monotherapy. In some embodiments, the composition consists essentially of an effective amount of linaclotide. In some embodiments, the composition consists of an effective amount of linaclotide.

In some embodiments, the compositions are directly administered to a patient, for example, in the form of a capsule, tablet or orally-disintegrating composition (e.g., orally-disintegrating tablet or film). In some embodiments, the compositions are dissolved, disintegrated and/or mixed on or within food or beverage prior to administration to patients (e.g., elderly or pediatric patients). In some embodiments, the composition is dissolved or disintegrated in a liquid, solution, or fluid optionally containing stabilizing agent(s), preservative(s), sweetener(s), or the like, etc. prior to administration to a patient (e.g., elderly or pediatric patient).

In some embodiments, the composition is a multiple dose composition, i.e., containing two, three, five, seven, ten, fifteen, twenty, twenty-five, thirty, forty, fifty, sixty, seventy, eighty, ninety or more daily doses of linaclotide. In some embodiments, one or more orally-disintegrating tablets or films containing 3.5 µg of linaclotide are dissolved or disintegrated within a liquid, solution or fluid to provide a composition that contains a five day supply of 0.5 µg of linaclotide dosages of the composition ("a five dose composition"). In some embodiments, one or more orally-disintegrating tablets or films containing 15 µg of linaclotide are dissolved or disintegrated within a liquid, solution, or fluid to provide a composition that contains a thirty day supply of 0.5 µg of linaclotide dosages of the composition ("a thirty dose composition"). In some embodiments, one or more orally-disintegrating tablets or films containing 45 µg of linaclotide are dissolved or disintegrated within a liquid, solution, or fluid to provide a composition that contains a ninety day supply of 0.5 µg of linaclotide dosages of the composition ("a ninety dose composition"). In some embodiments, one or more orally-disintegrating tablets or films containing 60 µg of linaclotide are dissolved or disintegrated within a liquid, solution, or fluid to provide a composition that contains a 120 day supply of 0.5 µg of linaclotide dosages of the composition ("a 120 dose composition").

In some embodiments, one or more orally-disintegrating tablets or films containing 90 µg of linaclotide are dissolved or disintegrated within a liquid, solution, or fluid to provide a composition that contains a 180 day supply of 0.5 µg of linaclotide dosages of the composition ("a 180 dose composition").

In other embodiments, the compositions are administered as part of a combination therapy. For example, a composition may be used in combination with other drugs or therapies that are used in the treatment, prevention, suppression, and/or amelioration of the diseases or conditions for which compounds of the invention are useful. The linaclotide can be co-administered or co-formulated with other medications. In one embodiment, the linaclotide composition can be co-administered with other medications used to treat gastrointestinal disorders including but not limited to acid suppressing agents such as Histamine-2 receptor agonists (H2As) and/or proton pump inhibitors (PPIs).

Such other drug(s) may be administered, by a route and in an amount commonly used therefore, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active components, in addition to a compound of invention.

Several methods can be used for evaluating the bioactivity of the linaclotide composition, including, but not limited to, immunoassays (e.g., enzyme-linked immunosorbent assay), radioimmuno assays, immunoradiometric assays, gel electrophoresis (e.g., SDS-PAGE), high performance liquid chromatography (HPLC), and/or high performance capillary electrophoresis (HPCE). In some embodiments, the bioactivity of the composition is assessed by a method comprising fixing linaclotide, incubating linaclotide with guanylate cyclase C (GCC), incubating GCC bound linaclotide with antibodies against GCC, incubating GCC antibody-bound linaclotide with fluorescently labeled antibodies against GCC antibodies, and detecting the linaclotide bound to the GCC antibodies by measuring the fluorescence intensity using a plate reader. The drug concentration can then be calculated based on the fluorescence reading of the solution.

For example, the bioactivity of the linaclotide compositions can be assessed and quantified using the following method, although other methods are available. The composition is added to a volumetric flask containing 60 ml of phosphate buffer having a pH of 4.5, and the flask is shaken for 60 minutes. 0.2 ml of the supernatant is then removed, and is added into one or more wells of a 96-well plate that is coated with GCC. The plate is sealed and incubated at 37° C. for 2 hr. At the end of incubation, the sample is removed and the plate is washed with phosphate buffered saline (PBS). The bound linaclotide is then incubated for 1 hour, at room temperature, with GCC (such as is available from Sigma-Aldrich Inc.) labeled with fluorescein isocyanate (FITC) in blocking buffer. After incubation, the well is washed with PBS. The fluorescence intensity of the end product is detected, for example, by using a plate reader. The linaclotide concentration is then calculated based on the fluorescence reading of the solution.

Definitions

Linaclotide is a peptide that consists of the amino acid sequence $Cys_1$ $Cys_2$ $Glu_3$ $Tyr_4$ $Cys_5$ $Cys_6$ $Asn_7$ $Pro_8$ $Ala_9$ $Cys_{10}$ $Thr_{11}$ $Gly_{12}$ $Cys_{13}$ $Tyr_{14}$ (SEQ ID NO:1). Linaclotide can exist in free form or in the form of a pharmaceutically acceptable salt or hydrate.

As used herein, unless otherwise indicated, the term "entry into a use environment" means contact of the composition with saliva of the patient to whom it is administered, or with a fluid intended to simulate saliva, e.g., having a pH greater than 5, or with a phosphate buffer solution having a pH of 4.5 and maintained at 37±1° C.

The term "released from", when referring to the release of linaclotide from the composition, unless otherwise indicated, is used herein to mean that the linaclotide no longer remains in a composition form.

As used herein, unless otherwise indicated, "stabilizing agent" refers to a polymer, sterically hindered primary amine (e.g., amino acid), or cation (e.g., metal cation) component of the composition which is included in the composition in a stabilizing amount. For example, a polymeric stabilizing agent is a polymer that is included in the composition in a stabilizing amount. Similarly, a sterically hindered primary amine stabilizing agent is a sterically hindered primary amine that is included in the composition in a stabilizing amount. Moreover, a cationic stabilizing agent is a cation that is included in the composition in a stabilizing amount.

As used herein, unless otherwise indicated, "stabilizing amount" refers to a concentration, within the composition, of a polymer, sterically hindered primary amine (e.g., amino acid), or metal cation component at which the component increases the stability of linaclotide in the composition, as compared to a similar composition not having a stabilizing amount of the same component.

As used herein, unless otherwise indicated, a "low-dose pharmaceutical composition" is a pharmaceutical composition that comprises less than 125 µg of linaclotide, for example less than 110 µg, less than 100 µg, less than 80 µg, less than 70 µg, less than 60 µg, or even less than 50 µg of linaclotide (for example, between 0.001 µg and 125 µg, between 0.001 µg and 100 µg, between 0.001 µg and 80 µg, or between 0.001 µg and 50 µg of linaclotide).

As used herein, unless otherwise indicated, the term "substantially all" means at least about 90%, for example, at least about 95% or even at least about 99%.

As used herein, unless otherwise indicated, the term "isolated and purified" means at least 95 percent pure (for example, at least 96% pure, at least 97% pure, at least 98% pure, or even at least 99% pure), as measured, for example, by chromatographic purity using HPLC.

As used herein, unless otherwise indicated, "therapeutically effective amount" means the amount of a linaclotide or a pharmaceutically acceptable salt thereof that, when administered to a mammal for treating a state, disorder or condition, is sufficient to effect a treatment (as defined below). The "therapeutically effective amount" will vary depending on the compound, the disease and its severity and the age, sex, weight, physical condition and responsiveness of the mammal to be treated. For example, a therapeutically effective amount of linaclotide, or its pharmaceutically acceptable salt or hydrate, can be an amount effective to treat gastrointestinal disorders, including irritable bowel syndrome, constipation-predominant irritable bowel syndrome, chronic constipation, opioid induced constipation and/or dyspepsia.

As used herein, unless other indicated, "pharmaceutically acceptable" means biologically or pharmacologically compatible for in vivo use in animals or humans, and preferably means, approved by a regulatory agency of the Federal or a state government or listed in the U.S. Pharmacopeia or other generally recognized pharmacopeia for use in animals, and more particularly in humans.

As used herein, unless otherwise indicated, the term "treat", in all its verb forms, is used herein to mean to relieve, alleviate, prevent, and/or manage at least one symptom of a disorder in a subject, the disorder including, for example, a gastrointestinal disorder, such as, irritable bowel syndrome, constipation-predominant irritable bowel syndrome, chronic constipation, opioid induced constipation, dyspepsia, or a combination of symptoms thereof. Within the meaning of the present invention, the term "treat" also denotes, to arrest, delay the onset (i.e., the period prior to clinical manifestation of a disease) and/or reduce the risk of developing or worsening a disease. The term "treatment" means the act of "treating" as defined above.

As used herein, unless otherwise indicated, the term "additives" refers to a pharmaceutically acceptable additive. Pharmaceutically acceptable additives include, without limitation, binders, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes.

As used herein, unless otherwise indicated, an "excipient" is any pharmaceutically acceptable additive, filler, binder or agent.

As used herein, unless otherwise indication, "stressed conditions" refer to 40° C. and 75% relative humidity (RH).

As used here, unless otherwise indicated, the terms "about" and "approximately" mean within an acceptable error range for the particular value as determined by one of ordinary skill in the art, which will depend, in part, on how the value is measured or determined, i.e., the limitations of the measurement system. For example, "about" can mean within 1 or more than 1 standard deviation, per practice in the art. Alternatively, "about" with respect to the compositions can mean plus or minus a range of up to 20%, preferably up to 10%. Alternatively, particularly with respect to biological systems or processes, the term can mean within an order of magnitude, preferably within 5-fold, and more preferably within 2-fold, of a value. Particular values are described in the application and claims, unless otherwise stated the term "about" means within an acceptable error range for the particular value.

All weight percentages (i.e., "% by weight" and "wt. %" and w/w) referenced herein, unless otherwise indicated, are measured relative to the total weight of the pharmaceutical composition.

The term "consisting essentially of", and variants thereof, when used to refer to the composition, are used herein to mean that the composition includes linaclotide and other desired pharmaceutically inactive additives, excipients, and/ or components (e.g., polymers, sterically hindered primary amines, cations, filling agents, binders, carriers, excipients, diluents, disintegrating additives, lubricants, solvents, dispersants, coating additives, absorption promoting additives, hydrolysis products, formaldehyde imine products, oxidation products, acetylation products, deamidation products, multimers, controlled release additives, anti-caking additives, anti-microbial additives, preservatives, sweetening additives, colorants, flavors, desiccants, plasticizers, dyes, or the like), and no other active pharmaceutical ingredient(s).

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

The following tests were employed in the examples section, unless otherwise indicated:

1) Stability of Linaclotide Compositions.

For stability evaluation, linaclotide compositions (0.15 mg theoretical, actual 0.135 mg) were packaged into a HDPE bottle with desiccant, and stored under at 40° C. and 75% RH ("stressed conditions"). The amount of linaclotide was assayed initially and after up to 18 months of storage at stressed conditions. The concentration of linaclotide was analyzed and quantified using an HPLC method with the following mobile phase gradient: Mobile phase A: 50 mM of sodium perchlorate in a solvent containing 76% water and 24% acetonitrile and 0.1% of trifluoroacetic acid; Mobile phase B: 50 mM of sodium perchlorate in a solvent containing 5% water and 95% acetonitrile and 0.1% of trifluoroacetic acid; Flow rate: 0.6 ml/min; Column: YMC Pro C18, 150 mm×3 mm ID, 3 µm or equivalent; Column temperature: 40° C.; Fluorescence detection: excitation: 274 nm; emission: 303 nm; Injection volume: 100 µl. 2) Analysis of total degradants in the pharmaceutical composition: Degradant analysis was performed using an HPLC method employing the following conditions: Mobile phase A: Water: acetonitrile 98:2, with 0.1% (v/v) of trifluoroacetic acid; Mobile phase B: Water:acetonitrile 5:95, with 0.1% (v/v) of trifluoroacetic acid; Flow rate: 0.6 ml/min; Column: YMC Pro C, 18, 150 mm×3 mm ID, 3 µm or equivalent; Column temperature: 40° C.; UV detection: excitation: 220 nm; Injection volume: 50 µl. The percentage amounts of degradants in the composition were calculated by quantifying the area of all peaks in the HPLC chromatogram to obtain the "total peak area", and dividing the peak area of each degradant by the total peak area. Specific degradants assayed include, for example, the hydrolysis product, Asp-7.

Example 1

Linaclotide beads were prepared in the following manner using the components set forth in Table 1. First, a linaclotide solution was prepared by combining linaclotide, polyvinyl alcohol, calcium chloride, meglumine and water in the concentrations set forth in Table 1. The linaclotide solution was then pH-adjusted to about 2.5 and mixed until clear. Next, the linaclotide solution was layered onto isomalt beads by spraying the beads with the linaclotide solution using a Wurster process. The linaclotide-layered beads were then dried until the product loss on drying (LOD) was less than about 3%.

TABLE 1

Linaclotide beads, 5 µg/50 mg

| Components | Weight (g) | Wt. % |
|---|---|---|
| Linaclotide | 0.24 | 0.012 |
| Isomalt | 1915 | 95.8 |
| Meglumine | 2.6 | 0.1 |
| Calcium chloride dihydrate | 2.0 | 0.1 |
| PVA | 80 | 4 |
| HCl | Q.S. | QS |
| Purified water* | 1000 | QS |
| TOTAL | 2000 | 100.0 |

*Water is removed during the manufacturing process

The stability performance of the linaclotide beads were assessed following storage of the beads for 1 month at 40° C. and 75% RH in 45 cc HDPE bottles (induction sealed and not containing desiccant). Results of the stability performance assay are set forth in Table 2.

TABLE 2

Results of stability performance assay

| Time | Asp-7 Degradant | Imine Degradant | Purity % |
|---|---|---|---|
| initial | 0.11 | <0.1 | 97.8 |
| 1 wk | 0.25 | 0.11 | 96.5 |
| 2 wk | 0.31 | <0.1 | 96.5 |
| 1 m | 0.37 | <0.1 | 92.6 |

Example 2

Linaclotide beads were prepared in the following manner using the components set forth in Table 3. First, a linaclotide solution was prepared by combining linaclotide, polyvinyl alcohol, calcium chloride, histidine and water in the concentrations set forth in Table 3. The linaclotide solution was then pH-adjusted to about 2.5 and mixed until clear. Next, the linaclotide solution was layered onto isomalt beads by spraying the beads with the linaclotide solution using a Wurster process. The linaclotide-layered beads were then dried until the product loss on drying (LOD) was less than about 3%.

TABLE 3

Linaclotide beads, 5 µg/50 mg

| Components | Weight (g) | Wt. % |
|---|---|---|
| Linaclotide | 0.24 | 0.012 |
| Isomalt | 1916 | 95.8 |
| Histidine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 3

Linaclotide beads were prepared in the manner described in Example 2 using the components set forth in Table 4.

TABLE 4

Linaclotide beads, 5 µg/50 mg

| Components | Weight (g) | Wt. % |
|---|---|---|
| Linaclotide | 0.24 | 0.012 |
| Isomalt | 1916 | 95.8 |
| Leucine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 4

Linaclotide beads were prepared in the manner described in Example 2 using the components set forth in Table 5.

TABLE 5

Linaclotide beads, 5 µg/50 mg

| Components | Weight (g) | Wt. % |
|---|---|---|
| Linaclotide | 0.24 | 0.012 |
| Isomalt | 1916 | 95.8 |
| Arginine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 5

Linaclotide beads were prepared in the manner described in Example 2 using the components set forth in Table 6.

TABLE 6

Linaclotide beads, 5 µg/50 mg

| Components | Weight (grams) | Wt. % |
|---|---|---|
| Linaclotide | 0.24 | 0.012 |
| Isomalt | 1916 | 95.8 |
| Lysine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 6

The stability and dissolution performance were assessed for the linaclotide beads prepared in Examples 2-5 following storage of the beads at 40° C. and 75% RH in HDPE bottles (sealed with heat and not containing desiccant). Results of the stability and dissolution performance assays are set forth in Tables 7-8 and FIG. 1 (which illustrates imine degradant concentrations).

TABLE 7

Stability of linaclotide beads at 40° C., 75% RH

| | Assay (normalized) | | |
|---|---|---|---|
| Amino acid | 1 wk | 2 wk | 1 mo |
| Histidine | 96.5 | 99.7 | 93.1 |
| Leucine | 95.9 | 95.2 | 93.5 |
| Lysine | 92.5 | 91.4 | 87.6 |
| Arginine | 96.9 | 92.5 | 89.5 |

TABLE 8

Degradation profile of linaclotide beads at 40° C., 75% RH

| Amino acid | Duration of Storage | Asp-7 Degradant | Imine Degradant | Purity |
|---|---|---|---|---|
| Histidine | initial | 0.18 | 0.16 | 98.3 |
|  | 1 wk | 0.11 | 0.27 | 98.3 |
|  | 2 wk | 0.15 | 0.41 | 96.5 |
|  | 1 mo | 0.26 | 0.61 | 93.4 |
| Leucine | initial | — | 0.18 | 97.6 |
|  | 1 wk | 0.17 | 0.79 | 96.9 |
|  | 2 wk | 0.19 | 1.00 | 94.8 |
|  | 1 mo | 0.20 | 1.92 | 90.7 |
| Lysine | initial | 0.17 | 0.24 | 97.5 |
|  | 1 wk | 0.12 | 1.74 | 94.8 |
|  | 2 wk | 0.18 | 2.57 | 92.0 |
|  | 1 mo | 0.14 | 3.64 | 85.9 |
| Arginine | initial | 0.10 | 0.14 | 98.9 |
|  | 1 wk | 0.18 | 1.41 | 95.7 |
|  | 2 wk | 0.28 | 2.12 | 92.8 |
|  | 1 mo | 0.24 | 2.55 | 88.6 |

Example 7

Linaclotide beads may be prepared in the manner described in Example 2 using the components set forth in Table 9.

TABLE 9

Linaclotide beads, 5 μg/50 mg

| Components | Weight (g) | Wt % |
|---|---|---|
| Linaclotide | 0.24 | 0.012 |
| Isomalt | 1916 | 95.8 |
| Melamine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 8

Linaclotide beads may be prepared in the manner described in Example 2 using the components set forth in Table 10.

TABLE 10

Linaclotide beads, 5 μg/50 mg

| Components | Weight (g) | Wt % |
|---|---|---|
| Linaclotide | 0.24 | 0.012 |
| Isomalt | 1916 | 95.8 |
| Gelatin | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 9

Linaclotide beads may be prepared in the manner described in Example 2 using the components set forth in Table 11.

TABLE 11

Linaclotide beads, 5 μg/50 mg

| Components | Weight (g) | Wt % |
|---|---|---|
| Linaclotide | 0.24 | 0.012 |
| Isomalt | 1916 | 95.8 |
| Glycine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 10

Linaclotide beads may be prepared in the manner described in Example 2 using the components set forth in Table 12.

TABLE 12

Linaclotide beads, 5 μg/50 mg

| Components | Weight (g) | Wt % |
|---|---|---|
| Linaclotide | 0.24 | 0.012 |
| Isomalt | 1916 | 95.8 |
| Glycine-Leucine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 11

Linaclotide beads may be prepared in the manner described in Example 2 using the components set forth in Table 13.

TABLE 13

Linaclotide beads, 5 μg/50 mg

| Components | Weight (g) | Wt % |
|---|---|---|
| Linaclotide | 0.24 | 0.012 |
| Isomalt | 1916 | 95.8 |
| Leucine-Glycine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 12

Linaclotide beads may be prepared in the manner described in Example 2 using the components set forth in Table 14.

TABLE 14

Linaclotide beads, 5 μg/50 mg

| Components | Weight (g) | Wt % |
|---|---|---|
| Linaclotide | 0.24 | 0.012 |
| Isomalt | 1916 | 95.8 |
| Albumin | 2 | 0.1 |
| Calcium chloride dehydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

Example 13

Linaclotide beads were prepared in the manner described in Example 2 using the components set forth in Table 15.

TABLE 15

Linaclotide beads, 5 μg/50 mg

| Components | Weight (g) | Wt. % |
|---|---|---|
| Linaclotide | 0.24 | 0.012 |
| Isomalt | 1916 | 95.8 |
| Asparagine | 2 | 0.1 |
| Calcium chloride dihydrate | 2.0 | 0.1 |
| PVA | 80 | 4 |
| HCl | Q.S. | — |
| Purified water* | 1000 | — |
| TOTAL | 2000 | 100.0 |

*Water is removed during the manufacturing process

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

All patents, patent applications, publications, product descriptions, and protocols are cited throughout this application, the disclosures of which are incorporated herein by reference in their entireties for all purposes.

SEQUENCE LISTING

```
<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 2

Cys Cys Glu Tyr Cys Cys Asp Pro Ala Cys Thr Gly Cys Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
```

```
<222> LOCATION: (1)..(1)
<223> OTHER INFORMATION: Formaldehyde bonded to Cys1
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 3

Cys Cys Glu Tyr Cys Cys Asn Pro Ala Cys Thr Gly Cys Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<223> OTHER INFORMATION: Cys1 is oxidized.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 4

Cys Cys Glu Tyr Cys Cys Asn Pro Ala Cys Thr Gly Cys Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MISC_FEATURE
<222> LOCATION: (1)..(1)
<223> OTHER INFORMATION: Xaa1 is a Cys, wherein the alpha-amine of the
      Cys which is cross-linked to the amine group of Cys2 to form an
      imidazolidinone 5 membered ring at the N-terminus of the peptide.
<220> FEATURE:
<221> NAME/KEY: DISULFID
<222> LOCATION: (1)..(6)
<223> OTHER INFORMATION: Disulfide bond is between the imidazolidinone
      5-membered ring of Xaa1 and Cys6.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 5

Xaa Cys Glu Tyr Cys Cys Asn Pro Ala Cys Thr Gly Cys Tyr
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 6

Cys Cys Glu Tyr Cys Cys Asn Pro Ala Cys Thr Gly Cys Tyr
1               5                   10
```

What is claimed is:

1. A method of treating a gastrointestinal disorder in a patient, the method comprising administering to a patient in need thereof, a pharmaceutical composition comprising linaclotide, $Ca^{2+}$ or pharmaceutically acceptable salt thereof and histidine, wherein the composition has a molar ratio of $Ca^{2+}$:histidine of less than 1.5:1 and a molar ratio of histidine:linaclotide is between 120:1 and 80:1, wherein the gastrointestinal disorder is selected from the group consisting of irritable bowel syndrome, chronic constipation, and opioid induced constipation.

2. The method of claim 1, wherein the gastrointestinal disorder is chronic constipation.

3. The method of claim 1, wherein the irritable bowel syndrome is constipation-predominant irritable bowel syndrome.

4. The method of claim 1, wherein the molar ratio of $Ca^{2+}$:histidine is between about 1.3:1 and 0.7:1.

5. The method of claim 4, wherein the molar ratio of $Ca^{2+}$:histidine is between about 1.1:1 and 0.9:1.

6. The method of claim 1, wherein the molar ratio of $Ca^{2+}$:histidine is 0.5:1.

7. The method of claim 1, wherein the pharmaceutical composition has a molar ratio of $Ca^{2+}$:linaclotide is about 50:1.

8. The method of claim 1, wherein the molar ratio histidine:linaclotide is about 100:1.

9. The method of claim 1, wherein the molar ratio of histidine:linaclotide is between 110:1 and 90:1 and the molar ratio of $Ca^{2+}$:linaclotide is between 60:1 and 20:1.

10. The method of claim 1, wherein the composition further comprises a polymer.

11. The method of claim 10, wherein the polymer is selected from the group consisting of polyvinyl pyrrolidone (PVP), polyvinyl alcohol (PVA) and a mixture thereof.

12. The method of claim 11, wherein the polymer is polyvinyl alcohol (PVA).

13. The method of claim 12, wherein the composition comprises 1% to 5% by weight of polyvinyl alcohol (PVA).

14. The method of claim 12, wherein the composition comprises 1.5% by weight of polyvinyl alcohol (PVA).

15. The method of claim 1, wherein the composition comprises 0.001 μg to 300 μg of linaclotide.

16. The method of claim 15, wherein the composition comprises 25 μg to 75 μg of linaclotide.

17. The method of claim 16, wherein the composition comprises 50 μg to 75 μg of linaclotide.

18. The method of claim 1, wherein the composition comprises 50 μg to 300 μg of linaclotide.

19. The method of claim 18, wherein the composition comprises 300 μg of linaclotide.

20. The method of claim 1, wherein the molar ratio of histidine to linaclotide is about 100:1, a molar ratio of Ca2+ to linaclotide is about 50:1 and the composition further comprises polyvinyl alcohol (PVA).

* * * * *